(12) United States Patent
Bozyczko-Coyne et al.

(10) Patent No.: US 6,310,040 B1
(45) Date of Patent: Oct. 30, 2001

(54) TREATING RETINAL NEURONAL DISORDERS BY THE APPLICATION OF INSULIN-LIKE GROWTH FACTORS AND ANALOGS

(75) Inventors: Donna Bozyczko-Coyne, Norristown; Nicola Neff, Wallingford; Michael E. Lewis, West Chester; Mohamed A. Iqbal, Malvern, all of PA (US)

(73) Assignee: Cephalon, Inc., West Chester, PA (US)

(*) Notice: Subject to any disclaimer, the term of this patent is extended or adjusted under 35 U.S.C. 154(b) by 0 days.

(21) Appl. No.: 07/963,329

(22) Filed: Oct. 15, 1992

Related U.S. Application Data

(63) Continuation-in-part of application No. 07/790,690, filed on Nov. 8, 1991, now abandoned.

(51) Int. Cl.$^7$ .......................... A61K 38/00; A61K 38/28; A61K 35/30; C07K 16/00

(52) U.S. Cl. .................................... 514/12; 514/3; 514/4; 514/21; 514/912; 424/570; 530/839; 530/303

(58) Field of Search ............................... 514/12, 3, 4, 21, 514/912; 424/570; 530/839, 303

(56) References Cited

U.S. PATENT DOCUMENTS

| | | | |
|---|---|---|---|
| 4,783,524 | 11/1988 | Larsen et al. | ........................ 530/350 |
| 5,068,224 | * 11/1991 | Fryklund et al. | ....................... 514/21 |
| 5,077,276 | * 12/1991 | Ballard et al. | .......................... 514/12 |
| 5,093,317 | * 3/1992 | Lewis et al. | ............................. 514/12 |

FOREIGN PATENT DOCUMENTS

| | | | |
|---|---|---|---|
| 0227619 | * 7/1987 | (EP) | ................................ C07K/7/10 |
| 0 227 619 | 7/1987 | (EP) | ................................ C07K/7/10 |
| 0 289 314 | 11/1988 | (EP) | ............................. A61K/37/36 |
| 0 308 386 | 3/1989 | (EP) | ................................ A61K/37/36 |
| WO89/05822 | 6/1989 | (WO) | ............................... C07K/7/10 |
| PCT/US92/ 09443 | 6/1992 | (WO) | ............................. A01K/37/02 |
| 9302695 | * 2/1993 | (WO) | ............................. A61K/37/02 |

OTHER PUBLICATIONS

Goldstein etal (1986) Scientific Amer. 255: 74–83.*
Kandel etal (eds) "Principles of Neurol Science" Elsevier, New York, (1991), pp. 298,299,342–343,389–390,401–403, & 539–540.*
Zackenfels etal (1993) Ann.N.Y. Acad.Sci. 692:302–304.*
Hedrich, H.J. (ed.) (1990) "Genetic Monitoring of Inbred Strains of Rats", Gustav Fischer Verlag, New York,pp. 440–441.*
Lolley etal (1991) In "Retinal Degenerations" (J.G. Hollyfield, eds), CRC Press, Inc., Boca Raton, Florida, pp. 5–12.*
Daughaday etal (1989) Endocrine Reviews10(1): 68–91.*
La Vail et al (1992) Proc. Nat'l. Acad Sci. 89: 11249–11253.*
Faktorovich etal (1992) J. Neurosic. 12(9): 3554–3567.*
La Vail etal (1987) Invest. Opthomol. 28: 1043–1048.*
Hicks etal (1987) J. Histochem. Cytochem. 35: 1317–1328.*
Robbins etal (1993) J. Neurosci. (19,Part1) : 656.*
"Physicians Desk Reference for Opthalmology" (1992), pp. 3–8.*
Strong etal (1993), Ann. N.Y. Acad.Sci. 692:317–320.*
Miller etal (1986) Trends in Neurosci. (Volume Not Given) pp. 211–218.*
Guyton, A.C. (1987) "Basic Neuroscience," Harcourt Brace Jovanovich, Inc., Philadelphia, p. 162.*
Ocrant et al. (1989) Endocrinology 125(5): 2407–2413.*
Lesson et al (1976) "Histology" W.B. Saunders Co., Philadelphia, pp. 554–565.*
Fellows et al. (1987) Soc. Neurosci. Abstr. 13:1615.*
Hansson et al (1986) Acta Physiol. Scand. 126:609–614.*
Waldbillig etal (1988) Exp. Eye Res 47: 587–607.*
Zick etal (1987) J. Biol. Chem. 262:10259–10264.*
Waldbillig etal (1991) J. Neurochem 57: 1522–1533. (Issued Oct. 15).*
Yorek etal (1987) J. Biol. Chem. 262(22):10986–10993.*
Bozyczko–Coyne etal (1993) Ann. N.Y. Acad.Sci. 692:311–313.*
Bozyczko–Coyne etal (1993)Soc. Neurosci.Abstr. 19(1) :653.*
Bozyczko–Coyne etal (1993)Soc.Neurosci. Abstr. 19(1) : 656.*
Fingl et al (1975) In L.S.Goodman etal (Eds.) "The Pharmacological Basis of Therapeutics", Macmillian Publishing Co., Inc., New York, pp. 1–46.*
Leschey etal (1990) Invest. Opthal. Vis. Sci. 31(5) :839–846.*
Nilsson etal (1988) Neurosci. Lett. 88: 221–226.*
Kanje etal (1989) Brain Res. 486 : 396–398.*
Lynch Et Al., Proc. Natl. Acad. Sci., vol. 84, Issued Nov. 1987, pp. 7696–7700.
Aizeman et al., Brain Research 406:32–42 (1987), "Brain neurons develop in a serum and glial free environment: effects of transferrin, insulin, insulin–like growth factor–I and thyroid hormone . . . ".
Ballard et al., Biochem. J. 249:721–726 (1988), "Specific binding of insulin–like growth factors 1 and 2 to the type 1 and type 2 receptors respectively".
Baskin et al., TINS 11(3):107–111 (1988), "Insulin and insulin–like growth factors in the CNS".

(List continued on next page.)

Primary Examiner—Yvonne Eyler
(74) Attorney, Agent, or Firm—Woodcock Washburn Kurtz Mackiewicz & Norris LLP

(57) ABSTRACT

Disclosed is a method for promoting retinal neuronal survival in a mammal, wherein the neuronal cells are at risk of dying. The method comprises administering to the mammal an effective dose of at least one of the following substances: IGF-I; a functional derivative of IGF-I; IGF-II; or a functional derivative of IGF-II.

1 Claim, 9 Drawing Sheets

OTHER PUBLICATIONS

Bassas et al., Endocrinology 125(5):2320–2327 (1989), "Development of Receptors for Insulin and Insulin–like Growth Factor–I in Head and Brain of Chick Embryos: Autoradiographic Localization".

Bassnett et al., Investigative Ophthalmology & Visual Science 31(8):1637–1643 (1990), "Localization of Insulin–like Growth Factor–1 Binding Sites in the Embryonic Chicken Eye".

Baxter, Comp. Biochem. Physiol. 91B(2):229–235 (1988), "The Insulin–Like Growth Factors and Their Binding Proteins".

Blundell et al., FASEB 42:2592–2597 (1983), "Tertiary structures, receptor binding, and antigenicity of insulinlike growth factors".

Bodor et al., Science 214:1370–1372 (1981), "Site–Specific, Sustained Release of Drugs to the Brain".

Bothwell, J. Neuorscience Res. 8:225–231 (1982), "Insulin and Somatomedin MSA Promote Nerve Growth Factor–Independent Neurite Formation by Cultured Chick Dorsal Root Ganglionic Sensory Neurons".

Bottenstein et al., Proc. Natl. Acad. Sci. USA 76(1):514–517 (1979), "Growth of a rat neuroblastoma cell line in serum–free supplemented medium".

Burgess et al., The Journal of Biological Chemistry 262(4):1618–1622 (1987), "Characterization of a Neuronal Subtype of Insulin–like Growth Factor I Receptor".

Creveling et al., Experientia 25:26–27 (1969), "Labile Lipophilic Derivatives of Norepinephrine Capable of Crossing the Blood–Brain Barrier".

Danias et al., Eye Research 9(4):379–386 (1990), "Express if IGF–I and IGF–II genes in the adult rat eye".

Daughaday et al., Endocrine Reviews 10(1):68–91 (1989), "Insulin–Like Growth Factors I And II. Peptide, Messenger Ribonucleic Acid and Gene Structures, Serum, and Tissue Concentrations".

D'Ercole, J. Developmental Physiology 9:481–495 (1987), "Somatomedins/insulin–like growth factors and fetal growth".

DiCicco–Bloom et al., Proc. Natl. Acad. Sci. USA 85:4066–4070 (1988), "Insulin growth factors regulate the mitotic cycle in cultured rat sympathetic neuroblasts".

Francis et al., Biochem J. 251:95–103 (1988), "Insulin–like growth factors 1 and 2 in bovine colostrum".

Francis et al., Art to Science in Tissue Culture, Hyclone Laboratories, Inc., vol. 11(1):3–7 (1992), "Long $R^3$ IGF–I—A Potent Insulin–like Growth Factor–I Analog That Supports Cell Growth".

Goodman et al., Accounts of Chemical Research 12(1):107 (1979), "One the Concept of Linear Modified Retro–Peptide Structures".

Grant et al., Diabetes 35:416–420 (1986), "Insulin–Like Growth Factors in Vitreous: Studies in Control and Diabetic Subjects with Neovascularization".

Hansson et al., Exp. Eyes Res. 48:411–420 (1989), "Changes in the Distribution of Insulin–like Growth Factor I, Thioredoxin, Thioredoxin Reductase and Ribonucleotide Reductase During the Development of the . . . ".

Hayward et al., Petptides 1974, Proceedings of the 13th European Peptide Symposium, Kiryat Anavim, Israel, Apr. 28–May 3, 1974, John Wily & Sons, Yecheskel Wolman, Ed., pp. 287–295, "The Effect of Reversal . . . ".

Hicks et al., The Journal of Histochemistry and Cytochemistry 35(11):1317–1328 (1987), "Different Rhodopsin Monoclonal Antibodies Reveal Different Binding Patterns on Development and Adult Rat Retina".

Karey et al., In Vitro Cellular & Developmental Biology 24(11):1107–1113 (1988), "Human Recombinant Insulin–like Growth Factor I. II. Binding Characterization and Radioreceptor Assay Development Using BALB/c 3T3 . . . ".

Kastin et al., Pharmacology Biochemistry & Behavior 11:713–716 (1979), "Analgesia After Peripheral Administration of Enkephalin and Endorphin Analogues".

King et al., J. Clin. Invest. 75:1028–1036 (1985), "Receptors and Growth–promoting Effects of Insulin and Insulinlike Growth Factors on Cells from Bovine Retinal Capillaries and Aorta".

Kumagai et al., J. Biological Chem. 262(31):15214–15219 (1987), "Absorptive–mediated Endocytosis of Cationized Albumin and a β–Endorphin–cationized Albumin Chimeric Peptide by Isolated Brain Capillaries".

Littlewood et al., Neoruochem. Int. 12(3):383–389 (1988), "Neuropeptides and Their Peptidases: Functional Considerations".

Maly et al., J. Biological Chem. 263(15):7068–7072 (1988), "The Binding Sites of Insulin–like Growth Factor I (IGF I) to Type I IGF Receptor and to a Monoclonal Antibody".

Massague et al., J. Biochem. Chem. 257:5038–5045 (1992), "The Subunit Structures of Two Distinct Receptors for Insulin–like Growth Factors I and II and Their Relationship to the Insulin Receptor".

Mattson et al., J. Cell Biology 102:1949–1954 (1986), "Mitogenic Response of Human SH–SY5Y Neuroblastoma Cells to Insulin–like Growth Factor I and II Is Dependent on the Stage of Differentiation".

McManaman et al., Neuron 4:891–898 (1990), "Rescue of Motoneurons from Cell Death by a Purified Skeletal Muscle Polypeptide: Effects of the ChAT Development Factor, CDF".

McMorris et al., J. Neurochemistry 44(4):1242–1251 (1985), "Induction of Myelin Components: Cyclic AMP Increases the Synthesis Rate of 2',3'–Cyclic Nucleotide 3'–Phosphohydrolases in $C_6$ Glioma Cells".

McMorris et al., J. Neuroscience Res. 21:199–209 (1988), "Insulin–Like Growth Factor I Promotes Cell Proliferation and Oligodendroglial Commitment in Rat Glial Progenitor Cells Developing In Vitro".

Mihara et al., Int. J. Peptide Protein 28:141–145 (1986), "Cyclic peptides: XXI. Syntheses of AM–toxin I analogs containing L–lactic acid or L–2–hydroxy–4–methylpentanoic acid residue".

Molday et al., Biochemistry 22:653–660 (1983), "Monoclonal Antibodies to Rhodopsin: Characterization, Cross–Reactivity, and Application as Structural Probes".

Nielsen et al., FEBS 262(1):142–144 (1990), "Mannose–6–phosphate stimulates proliferation of neuronal precursor cells".

Ocrant et al., Endocrinology 125(5):2407–2413 (1989), "Localization and Structural Characterization of Insulin–Like Growth Factor Receptors in Mammalian Retina".

Oppenheim et al., Science 251:1616–1617 (1991), "Control of Embryonic Motoneuron Survival in Vivo by Ciliary Neurotrophic Factor".

Pardridge et al., Biochem. Biophys. Res. Com. 146(1):307–313 (1987), "Chimeric Peptides as a Vehicle for Peptide Pharmaceutical Delivery Through the Blood–Brain Barrier".

Rapoport et al., Science 207:84–86 (1980), "Entry of Opioid Peptides into the Central Nervous System".

Rechler, Ann. Rev. Physiol. 47:425–442 (1985), "The Nature and Regulation of the Receptors for Insulin–Like Growth Factors".

Recio–Pinto et al., Proc. Natl. Acad. Sci. USA 81:2562–2566 (1984), "Insulin and insulin–like growth factor II permit nerve growth factor binding and the neurite formation response in cultured human neuroblastoma . . . ".

Recio–Pinto et al., J. Neuroscience Res. 19:312–320 (1988), "Insulin and Insulinlike Growth Factor Receptors Regulating Neurite Formation in Cultured Human Neuroblastoma Cells".

Recio–Pinto et al., J. Neuroscience 6(5):1211–1219 (1986), "Effects of Insulin, Insulin–like Growth Factor–II, and Nerve Growth Factor on Neurite Formation and Survival in Cultured Sympathetic and Sensory Neurons".

Riekkinen et al., Peptides 8:261–265 (1987), "Penetration of DGAVP (Org 5667) Across the Blood–Brain Barrier in Human Subjects".

Sara et al., Proc. Natl. Acad. Sci. USA 83:4904–4907 (1986), "Characterization of somatomedins from human fetal brain: Identification of a variant form of insulin–like growth factor I".

Shen et al., Proc. Natl. Acad. Sci. USA 75(4):1872–1876 (1978), "Conjugation of poly–L–lysine to albumin and horseradish peroxidase: A novel method of enhancing the cellular uptake of proteins".

Svrzic et al., Biochem. Biophys. Res. Com. 172(1):54–60 (1990), "Insulin–Like Growth Factor 1 Supports Embryonic Nerve Cell Survival".

Taylor et al., Drug Development Research 11:75–86 (1987), "Small Peptides and Nerve Growth: Therapeutic Implications".

Tollefsen et al., Biochemistry 30:48–54 (1991), "Interaction of the $\alpha\beta$ Dimers of the Insulin–like Growth Factor I Receptor Is Required for Receptor Autophosphorylation".

Torres–Aleman et al., Neuroscience 35(3):601–608 (1990), "Trophic Effects of Insulin–Like Growth Factor–I on Fetal Rat Hypothalamic Cells in Culture".

Tripathi et al., Drug Development Research 23:1–25 (1991), "Role of Growth Factors in the Uveal Tract of the Eye as Targeted to the Development of New Drugs".

Waldbillig et al., Exp. Eye Res. 47:587–607 (1988), "IGF–I Receptors in the Bovine Neural Retina: Structure, Kinase Activity and Comparison with Retinal Insulin Receptors".

Waldbillig et al., Exp. Eye Res. 53:13–22 (1991), "Insulin and IGF–I Binding in Developing Chick Neural Retina and Pigment Epithelium: A Characterization of Binding and Structural Differences".

Williams et al., Proc. Natl. Acad. Sci. USA 83:9231–9235 (1986), "Continuous infusion of nerve growth factor prevents basal forebrain neuronal death after fimbria fornix transection".

Williams et al., Proc. Natl. Acad. Sci. USA 78:2393–2397 (1981), "Micropinocytic ingestion of glycosylated albumin by isolated microvessels: Possible role in pathogenesis of diabetic microangiopathy".

Yorek et al., J. Biol. Chem. 262:10986–10993 (1987), "Amino Acid and Putative Neurotransmitter Transport in Human Y79 Retinoblastoma Cells".

Zetterstrom et al., J. Neurochemistry 57:1332–1339 (1991), "Characterization of a Novel Receptor in Toad Retina with Dual Specificity for Insulin and Insulin–Like Growth Factor I".

Zick et al., J. Biol. Chem. 262:10259–10264 (1987), "Insulin–like Growth Factor I Receptors in Retinal Rod Outer Segments".

* cited by examiner

```
                          SEQUENCE LISTING (1) GENERAL INFORMATION:

(iii) NUMBER OF SEQUENCES:    79

(2) INFORMATION FOR SEQ ID NO:    1:

(i) SEQUENCE CHARACTERISTICS:
        (A) LENGTH:               70
        (B) TYPE:                 amino acid
        (C) STRANDEDNESS:
        (D) TOPOLOGY:             linear (xi) SEQUENCE DESCRIPTION: SEQ ID NO: 1:

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
            20                  25                  30

Ser Ser Arg Arg Ala Pro Gln Thr Gly Ile Val Asp Glu Cys Cys
        35                  40                  45

Phe Arg Ser Cys Asp Leu Arg Arg Leu Glu Met Tyr Cys Ala Pro Leu
    50                  55                  60

Lys Pro Ala Lys Ser Ala
65                  70

(2) INFORMATION FOR SEQ ID NO:    2:
```

```
        (i) SEQUENCE CHARACTERISTICS:
            (A) LENGTH:           67
            (B) TYPE:             amino acid
            (C) STRANDEDNESS:
            (D) TOPOLOGY:         linear (xi) SEQUENCE DESCRIPTION: SEQ ID NO: 2:

Thr Leu Cys Gly Ala Glu Leu Val Asp Ala Leu Gln Phe Val Cys Gly
1               5                   10                  15

Asp Arg Gly Phe Tyr Phe Asn Lys Pro Thr Gly Tyr Gly Ser Ser Ser
            20                  25                  30

Arg Arg Ala Pro Gln Thr Gly Ile Val Asp Glu Cys Cys Phe Arg Ser
        35                  40                  45

Cys Asp Leu Arg Arg Leu Glu Met Tyr Cys Ala Pro Leu Lys Pro Ala
    50                  55                  60

Lys Ser Ala
65

(2) INFORMATION FOR SEQ ID NO:    3:

(i) SEQUENCE CHARACTERISTICS:
            (A) LENGTH:           18
            (B) TYPE:             amino acid
            (C) STRANDEDNESS:
            (D) TOPOLOGY:         linear (xi) SEQUENCE DESCRIPTION: SEQ ID NO: 3:

Tyr Phe Asn Lys Pro Thr Gly Tyr Gly Ser Ser Ser Arg Arg Ala Pro
1               5                   10                  15

Gln Thr (2) INFORMATION FOR SEQ ID NO:    4:

(i) SEQUENCE CHARACTERISTICS:
            (A) LENGTH:           12
            (B) TYPE:             amino acid
            (C) STRANDEDNESS:
            (D) TOPOLOGY:         linear (xi) SEQUENCE DESCRIPTION: SEQ ID NO: 4:

Gly Tyr Gly Ser Ser Ser Arg Arg Ala Pro Gln Thr
1               5                   10

(2) INFORMATION FOR SEQ ID NO:    5:

(i) SEQUENCE CHARACTERISTICS:
            (A) LENGTH:           9
            (B) TYPE:             amino acid
            (C) STRANDEDNESS:
            (D) TOPOLOGY:         linear (xi) SEQUENCE DESCRIPTION: SEQ ID NO: 5:

Ala Pro Leu Lys Pro Ala Lys Ser Ala
1               5

(2) INFORMATION FOR SEQ ID NO:    6:

(i) SEQUENCE CHARACTERISTICS:
            (A) LENGTH:           9
            (B) TYPE:             amino acid
            (C) STRANDEDNESS:
            (D) TOPOLOGY:         linear (xi) SEQUENCE DESCRIPTION: SEQ ID NO: 6:
```

```
Tyr Phe Asn Lys Pro Thr Gly Tyr Gly
1               5

(2) INFORMATION FOR SEQ ID NO:    7:

(i) SEQUENCE CHARACTERISTICS:
        (A) LENGTH:            18
        (B) TYPE:              amino acid
        (C) STRANDEDNESS:
        (D) TOPOLOGY:          linear (ix) FEATURE:
        (D) OTHER INFORMATION:    Xaa is a threonine with a carboxy-
            terminal amide group.

(xi) SEQUENCE DESCRIPTION: SEQ ID NO: 7:

Tyr Phe Asn Lys Pro Thr Gly Tyr Gly Ser Ser Ser Arg Arg Ala Pro
1               5                   10                  15

Gln Xaa (2) INFORMATION FOR SEQ ID NO:    8:

(i) SEQUENCE CHARACTERISTICS:
        (A) LENGTH:            9
        (B) TYPE:              amino acid
        (C) STRANDEDNESS:
        (D) TOPOLOGY:          linear (ix) FEATURE:
        (D) OTHER INFORMATION:    Xaa is a threonine with a carboxy-
            terminal amide group.

(xi) SEQUENCE DESCRIPTION: SEQ ID NO: 8:

Ser Ser Ser Arg Arg Ala Pro Gln Xaa
1               5

(2) INFORMATION FOR SEQ ID NO:    9:

(i) SEQUENCE CHARACTERISTICS:
        (A) LENGTH:            16
        (B) TYPE:              amino acid
        (C) STRANDEDNESS:
        (D) TOPOLOGY:          linear (ix) FEATURE:
        (D) OTHER INFORMATION:    Xaa at position 16 is a leucine
            with a carboxy-terminal amide
            group.  Xaa at position 7 is a
            cysteine with an acetamidomethyl-
            substituent on the side-chain.

(xi) SEQUENCE DESCRIPTION: SEQ ID NO: 9:

Gly Ile Val Asp Glu Cys Xaa Phe Arg Ser Cys Leu Asp Arg Arg Xaa
1               5                   10                  15

(2) INFORMATION FOR SEQ ID NO:    10:

(i) SEQUENCE CHARACTERISTICS:
        (A) LENGTH:            9
        (B) TYPE:              amino acid
        (C) STRANDEDNESS:
        (D) TOPOLOGY:          linear (xi) SEQUENCE DESCRIPTION: SEQ ID NO: 10:

Ser Ser Ser Arg Arg Ala Pro Gln Thr
1               5

(2) INFORMATION FOR SEQ ID NO:    11:
```

```
        (i) SEQUENCE CHARACTERISTICS:
              (A) LENGTH:           14
              (B) TYPE:             amino acid
              (C) STRANDEDNESS:
              (D) TOPOLOGY:         linear (xi) SEQUENCE DESCRIPTION: SEQ ID NO: 11:

Pro Thr Gly Tyr Gly Ser Ser Ser Arg Arg Ala Pro Gln Thr
1               5                   10

(2) INFORMATION FOR SEQ ID NO:    12:

(i) SEQUENCE CHARACTERISTICS:
              (A) LENGTH:           10
              (B) TYPE:             amino acid
              (C) STRANDEDNESS:
              (D) TOPOLOGY:         linear (xi) SEQUENCE DESCRIPTION: SEQ ID NO: 12:

Lys Pro Thr Gly Tyr Gly Ser Ser Ser Arg
1               5                   10

(2) INFORMATION FOR SEQ ID NO:    13:

(i) SEQUENCE CHARACTERISTICS:
              (A) LENGTH:           14
              (B) TYPE:             amino acid
              (C) STRANDEDNESS:
              (D) TOPOLOGY:         linear (xi) SEQUENCE DESCRIPTION: SEQ ID NO: 13:

Ala Leu Leu Glu Thr Tyr Cys Ala Thr Pro Ala Lys Ser Glu
1               5                   10

(2) INFORMATION FOR SEQ ID NO:    14:

(i) SEQUENCE CHARACTERISTICS:
              (A) LENGTH:           6
              (B) TYPE:             amino acid
              (C) STRANDEDNESS:
              (D) TOPOLOGY:         linear (xi) SEQUENCE DESCRIPTION: SEQ ID NO: 14:

Thr Pro Ala Lys Ser Glu
1               5

(2) INFORMATION FOR SEQ ID NO:    15:

(i) SEQUENCE CHARACTERISTICS:
              (A) LENGTH:           8
              (B) TYPE:             amino acid
              (C) STRANDEDNESS:
              (D) TOPOLOGY:         linear (xi) SEQUENCE DESCRIPTION: SEQ ID NO: 15:

Ser Arg Val Ser Arg Arg Ser Arg
1               5

(2) INFORMATION FOR SEQ ID NO:    16:

(i) SEQUENCE CHARACTERISTICS:
              (A) LENGTH:           67
              (B) TYPE:             amino acid
              (C) STRANDEDNESS:
              (D) TOPOLOGY:         linear (xi) SEQUENCE DESCRIPTION: SEQ ID NO: 16:

Ala Tyr Arg Pro Ser Glu Thr Leu Cys Gly Gly Glu Leu Val Asp Thr
```

```
1               5                   10                  15
Leu Gln Phe Val Cys Gly Asp Arg Gly Phe Tyr Phe Ser Arg Pro Ala
                20                  25                  30
Ser Arg Val Ser Arg Arg Ser Gly Ile Val Glu Glu Cys Cys Phe
            35                  40                  45
Arg Ser Cys Asp Leu Ala Leu Leu Glu Thr Tyr Cys Ala Thr Pro Ala
        50                  55                  60
Lys Ser Glu
65
```

(2) INFORMATION FOR SEQ ID NO:   17:

(i) SEQUENCE CHARACTERISTICS:
        (A) LENGTH:           16
        (B) TYPE:             amino acid
        (C) STRANDEDNESS:
        (D) TOPOLOGY:         linear (xi) SEQUENCE DESCRIPTION: SEQ ID NO: 17:

```
Cys Ala Leu Leu Glu Thr Tyr Cys Ala Thr Pro Ala Lys Ser Glu Cys
1               5                   10                  15
```

(2) INFORMATION FOR SEQ ID NO:   18:

(i) SEQUENCE CHARACTERISTICS:
        (A) LENGTH:           13
        (B) TYPE:             amino acid
        (C) STRANDEDNESS:
        (D) TOPOLOGY:         linear (xi) SEQUENCE DESCRIPTION: SEQ ID NO: 18:

```
Cys Gly Cys Glu Leu Val Asp Ala Leu Gln Phe Val Cys
1               5                   10
```

(2) INFORMATION FOR SEQ ID NO:   19:

(i) SEQUENCE CHARACTERISTICS:
        (A) LENGTH:           10
        (B) TYPE:             amino acid
        (C) STRANDEDNESS:
        (D) TOPOLOGY:         linear (xi) SEQUENCE DESCRIPTION: SEQ ID NO: 19:

```
Cys Asp Leu Arg Arg Leu Glu Met Tyr Cys
1               5                   10
```

(2) INFORMATION FOR SEQ ID NO:   20:

(i) SEQUENCE CHARACTERISTICS:
        (A) LENGTH:           15
        (B) TYPE:             amino acid
        (C) STRANDEDNESS:
        (D) TOPOLOGY:         linear (xi) SEQUENCE DESCRIPTION: SEQ ID NO: 20:

```
Cys Cys Phe Arg Ser Cys Asp Leu Arg Arg Leu Glu Met Tyr Cys
1               5                   10                  15
```

(2) INFORMATION FOR SEQ ID NO:   21:

(i) SEQUENCE CHARACTERISTICS:
        (A) LENGTH:           19
        (B) TYPE:             amino acid
        (C) STRANDEDNESS:
        (D) TOPOLOGY:         linear

```
    (xi) SEQUENCE DESCRIPTION: SEQ ID NO: 21:

Cys Asp Leu Arg Arg Leu Glu Met Tyr Cys Cys Pro Leu Lys Pro Ala
1               5                  10                  15

Lys Ser Glu (2) INFORMATION FOR SEQ ID NO:    22:

(i) SEQUENCE CHARACTERISTICS:
        (A) LENGTH:            6
        (B) TYPE:              amino acid
        (C) STRANDEDNESS:
        (D) TOPOLOGY:          linear (xi) SEQUENCE DESCRIPTION: SEQ ID NO: 22:

Cys Cys Phe Arg Ser Cys
1               5

(2) INFORMATION FOR SEQ ID NO:    23:

(i) SEQUENCE CHARACTERISTICS:
        (A) LENGTH:            5
        (B) TYPE:              amino acid
        (C) STRANDEDNESS:
        (D) TOPOLOGY:          linear (xi) SEQUENCE DESCRIPTION: SEQ ID NO: 23:

Cys Phe Arg Ser Cys
1               5

(2) INFORMATION FOR SEQ ID NO:    24:

(i) SEQUENCE CHARACTERISTICS:
        (A) LENGTH:            7
        (B) TYPE:              amino acid
        (C) STRANDEDNESS:
        (D) TOPOLOGY:          linear (xi) SEQUENCE DESCRIPTION: SEQ ID NO: 24:

Cys Ala Pro Ala Lys Ser Glu
1               5

(2) INFORMATION FOR SEQ ID NO:    25:

(i) SEQUENCE CHARACTERISTICS:
        (A) LENGTH:            9
        (B) TYPE:              amino acid
        (C) STRANDEDNESS:
        (D) TOPOLOGY:          linear (ix) FEATURE:
        (D) OTHER INFORMATION:    Xaa represents an iodinated
            tyrosine.

(xi) SEQUENCE DESCRIPTION: SEQ ID NO: 25:

Thr Xaa Cys Ala Pro Ala Lys Ser Glu
1               5

(2) INFORMATION FOR SEQ ID NO:    26:

(i) SEQUENCE CHARACTERISTICS:
        (A) LENGTH:            7
        (B) TYPE:              amino acid
        (C) STRANDEDNESS:
        (D) TOPOLOGY:          linear (xi) SEQUENCE DESCRIPTION: SEQ ID NO: 26:

Cys Gly Pro Glu Thr Leu Cys
```

```
1               5

(2) INFORMATION FOR SEQ ID NO:    27:

(i) SEQUENCE CHARACTERISTICS:
        (A) LENGTH:             19
        (B) TYPE:               amino acid
        (C) STRANDEDNESS:
        (D) TOPOLOGY:           linear (xi) SEQUENCE DESCRIPTION: SEQ ID NO: 27:

Cys Gly Tyr Gly Ser Ser Ser Arg Arg Cys Pro Gln Thr Gly Ile Val
1               5                   10                  15

Asp Glu Cys (2) INFORMATION FOR SEQ ID NO:    28:

(i) SEQUENCE CHARACTERISTICS:
        (A) LENGTH:             13
        (B) TYPE:               amino acid
        (C) STRANDEDNESS:
        (D) TOPOLOGY:           linear (xi) SEQUENCE DESCRIPTION: SEQ ID NO: 28:

Cys Gly Asp Arg Gly Phe Tyr Phe Asn Lys Pro Thr Cys
1               5                   10

(2) INFORMATION FOR SEQ ID NO:    29:

(i) SEQUENCE CHARACTERISTICS:
        (A) LENGTH:             11
        (B) TYPE:               amino acid
        (C) STRANDEDNESS:
        (D) TOPOLOGY:           linear (xi) SEQUENCE DESCRIPTION: SEQ ID NO: 29:

Cys Cys Pro Leu Lys Pro Ala Lys Ser Ala Cys
1               5                   10

(2) INFORMATION FOR SEQ ID NO:    30:

(i) SEQUENCE CHARACTERISTICS:
        (A) LENGTH:             19
        (B) TYPE:               amino acid
        (C) STRANDEDNESS:
        (D) TOPOLOGY:           linear (xi) SEQUENCE DESCRIPTION: SEQ ID NO: 30:

Cys Asp Leu Arg Arg Leu Glu Met Tyr Ala Pro Leu Lys Pro Ala
1               5                   10                  15

Lys Ser Ala Cys (2) INFORMATION FOR SEQ ID NO:    31:

(i) SEQUENCE CHARACTERISTICS:
        (A) LENGTH:             16
        (B) TYPE:               amino acid
        (C) STRANDEDNESS:
        (D) TOPOLOGY:           linear (xi) SEQUENCE DESCRIPTION: SEQ ID NO: 31:

Asp Leu Ala Leu Leu Glu Thr Tyr Ser Ala Thr Pro Ala Lys Ser Glu
1               5                   10                  15

(2) INFORMATION FOR SEQ ID NO:    32:
```

```
    (i) SEQUENCE CHARACTERISTICS:
        (A) LENGTH:           13
        (B) TYPE:             amino acid
        (C) STRANDEDNESS:
        (D) TOPOLOGY:         linear (xi) SEQUENCE DESCRIPTION: SEQ ID NO: 32:

Cys Gly Gly Glu Leu Val Asp Thr Leu Gln Phe Val Cys
1               5                   10

(2) INFORMATION FOR SEQ ID NO:   33:

(i) SEQUENCE CHARACTERISTICS:
        (A) LENGTH:           10
        (B) TYPE:             amino acid
        (C) STRANDEDNESS:
        (D) TOPOLOGY:         linear (xi) SEQUENCE DESCRIPTION: SEQ ID NO: 33:

Cys Asp Leu Cys Leu Leu Glu Thr Tyr Cys
1               5                   10

(2) INFORMATION FOR SEQ ID NO:   34:

(i) SEQUENCE CHARACTERISTICS:
        (A) LENGTH:           16
        (B) TYPE:             amino acid
        (C) STRANDEDNESS:
        (D) TOPOLOGY:         linear (xi) SEQUENCE DESCRIPTION: SEQ ID NO: 34:

Cys Cys Phe Arg Ser Cys Asp Asp Leu Ala Leu Leu Glu Thr Tyr Cys
1               5                   10                  15

(2) INFORMATION FOR SEQ ID NO:   35:

(i) SEQUENCE CHARACTERISTICS:
        (A) LENGTH:           17
        (B) TYPE:             amino acid
        (C) STRANDEDNESS:
        (D) TOPOLOGY:         linear (xi) SEQUENCE DESCRIPTION: SEQ ID NO: 35:

Cys Asp Leu Cys Leu Leu Glu Thr Tyr Cys Ala Thr Pro Ala Lys Ser
1               5                   10                  15
Glu (2) INFORMATION FOR SEQ ID NO:   36:

(i) SEQUENCE CHARACTERISTICS:
        (A) LENGTH:           15
        (B) TYPE:             amino acid
        (C) STRANDEDNESS:
        (D) TOPOLOGY:         linear (xi) SEQUENCE DESCRIPTION: SEQ ID NO: 36:

Glu Ala Leu Leu Glu Thr Tyr Cys Ala Thr Pro Ala Lys Ser Glu
1               5                   10                  15

(2) INFORMATION FOR SEQ ID NO:   37:

(i) SEQUENCE CHARACTERISTICS:
        (A) LENGTH:           14
        (B) TYPE:             amino acid
        (C) STRANDEDNESS:
        (D) TOPOLOGY:         linear (xi) SEQUENCE DESCRIPTION: SEQ ID NO: 37:
```

```
Ala Leu Leu Glu Lys Tyr Cys Ala Lys Pro Ala Lys Ser Glu
1               5                   10
```

(2) INFORMATION FOR SEQ ID NO:     38:

(i) SEQUENCE CHARACTERISTICS:
        (A) LENGTH:              9
        (B) TYPE:                amino acid
        (C) STRANDEDNESS:
        (D) TOPOLOGY:            linear (xi) SEQUENCE DESCRIPTION: SEQ ID NO: 38:

```
Ala Pro Ser Thr Cys Glu Tyr Lys Ala
1               5
```

(2) INFORMATION FOR SEQ ID NO:     39:

(i) SEQUENCE CHARACTERISTICS:
        (A) LENGTH:              15
        (B) TYPE:                amino acid
        (C) STRANDEDNESS:
        (D) TOPOLOGY:            linear (xi) SEQUENCE DESCRIPTION: SEQ ID NO: 39:

```
Cys Cys Phe Arg Ser Cys Asp Leu Cys Leu Leu Glu Thr Tyr Cys
1               5                   10                  15
```

(2) INFORMATION FOR SEQ ID NO:     40:

(i) SEQUENCE CHARACTERISTICS:
        (A) LENGTH:              10
        (B) TYPE:                amino acid
        (C) STRANDEDNESS:
        (D) TOPOLOGY:            linear (xi) SEQUENCE DESCRIPTION: SEQ ID NO: 40:

```
Cys Cys Tyr Arg Pro Ser Glu Thr Leu Cys
1               5                   10
```

(2) INFORMATION FOR SEQ ID NO:     41:

(i) SEQUENCE CHARACTERISTICS:
        (A) LENGTH:              18
        (B) TYPE:                amino acid
        (C) STRANDEDNESS:
        (D) TOPOLOGY:            linear (xi) SEQUENCE DESCRIPTION: SEQ ID NO: 41:

```
Cys Arg Pro Cys Ser Arg Val Ser Arg Arg Ser Arg Gly Ile Val Glu Glu
1               5                   10                  15
Cys
```

(2) INFORMATION FOR SEQ ID NO:     42:

(i) SEQUENCE CHARACTERISTICS:
        (A) LENGTH:              12
        (B) TYPE:                amino acid
        (C) STRANDEDNESS:
        (D) TOPOLOGY:            linear (xi) SEQUENCE DESCRIPTION: SEQ ID NO: 42:

```
Cys Gly Asp Arg Gly Phe Tyr Phe Ser Arg Pro Cys
1               5                   10
```

(2) INFORMATION FOR SEQ ID NO:     43:

```
    (i) SEQUENCE CHARACTERISTICS:
         (A) LENGTH:              9
         (B) TYPE:                amino acid
         (C) STRANDEDNESS:
         (D) TOPOLOGY:            linear (xi) SEQUENCE DESCRIPTION: SEQ ID NO: 43:

Cys Cys Thr Pro Ala Lys Ser Glu Cys
1               5

(2) INFORMATION FOR SEQ ID NO:    44:

(i) SEQUENCE CHARACTERISTICS:
         (A) LENGTH:              16
         (B) TYPE:                amino acid
         (C) STRANDEDNESS:
         (D) TOPOLOGY:            linear (xi) SEQUENCE DESCRIPTION: SEQ ID NO: 44:

Cys Asp Leu Cys Leu Leu Glu Thr Ala Thr Pro Ala Lys Ser Glu Cys
1               5                   10                  15

(2) INFORMATION FOR SEQ ID NO:    45:

(i) SEQUENCE CHARACTERISTICS:
         (A) LENGTH:              14
         (B) TYPE:                amino acid
         (C) STRANDEDNESS:
         (D) TOPOLOGY:            linear (ix) FEATURE:
         (D) OTHER INFORMATION:   Xaa represents the D-isomer of
             tyrosine.

(xi) SEQUENCE DESCRIPTION: SEQ ID NO: 45:

Ala Leu Leu Glu Thr Xaa Cys Ala Thr Pro Ala Lys Ser Glu
1               5                   10

(2) INFORMATION FOR SEQ ID NO:    46:

(i) SEQUENCE CHARACTERISTICS:
         (A) LENGTH:              10
         (B) TYPE:                amino acid
         (C) STRANDEDNESS:
         (D) TOPOLOGY:            linear (ix) FEATURE:
         (D) OTHER INFORMATION:   Xaa represents the D-isomer of
             tyrosine.

(xi) SEQUENCE DESCRIPTION: SEQ ID NO: 46:

Thr Xaa Cys Ala Thr Pro Ala Lys Ser Glu
1               5                   10

(2) INFORMATION FOR SEQ ID NO:    47:

(i) SEQUENCE CHARACTERISTICS:
         (A) LENGTH:              16
         (B) TYPE:                amino acid
         (C) STRANDEDNESS:
         (D) TOPOLOGY:            linear (ix) FEATURE:
         (D) OTHER INFORMATION:   Xaa represents the D-isomer of
             tyrosine.

(xi) SEQUENCE DESCRIPTION: SEQ ID NO: 47:

Cys Ala Leu Leu Glu Thr Xaa Cys Ala Thr Pro Ala Lys Ser Glu Cys
1               5                   10                  15
```

(2) INFORMATION FOR SEQ ID NO:   48:

(i) SEQUENCE CHARACTERISTICS:
        (A) LENGTH:           12
        (B) TYPE:             amino acid
        (C) STRANDEDNESS:
        (D) TOPOLOGY:         linear (ix) FEATURE:
        (D) OTHER INFORMATION:   Xaa represents the D-isomer of
            tyrosine.

(xi) SEQUENCE DESCRIPTION: SEQ ID NO: 48:

Cys Thr Xaa Cys Ala Thr Pro Ala Lys Ser Glu Cys
1               5                   10

(2) INFORMATION FOR SEQ ID NO:   49:

(i) SEQUENCE CHARACTERISTICS:
        (A) LENGTH:           11
        (B) TYPE:             amino acid
        (C) STRANDEDNESS:
        (D) TOPOLOGY:         linear (ix) FEATURE:
        (D) OTHER INFORMATION:   Xaa represents the D-isomer of
            tyrosine.

(xi) SEQUENCE DESCRIPTION: SEQ ID NO: 49:

Cys Thr Xaa Cys Ala Pro Ala Lys Ser Glu Cys
1               5                   10

(2) INFORMATION FOR SEQ ID NO:   50:

(i) SEQUENCE CHARACTERISTICS:
        (A) LENGTH:           9
        (B) TYPE:             amino acid
        (C) STRANDEDNESS:
        (D) TOPOLOGY:         linear (ix) FEATURE:
        (D) OTHER INFORMATION:   Xaa represents the D-isomer of
            tyrosine.

(xi) SEQUENCE DESCRIPTION: SEQ ID NO: 50:

Thr Xaa Cys Ala Pro Ala Lys Ser Glu
1               5

(2) INFORMATION FOR SEQ ID NO:   51:

(i) SEQUENCE CHARACTERISTICS:
        (A) LENGTH:           8
        (B) TYPE:             amino acid
        (C) STRANDEDNESS:
        (D) TOPOLOGY:         linear (xi) SEQUENCE DESCRIPTION: SEQ ID NO: 51:

Thr Tyr Cys Ala Thr Pro Ala Lys
1               5

(2) INFORMATION FOR SEQ ID NO:   52:

(i) SEQUENCE CHARACTERISTICS:
        (A) LENGTH:           8
        (B) TYPE:             amino acid
        (C) STRANDEDNESS:
        (D) TOPOLOGY:         linear (xi) SEQUENCE DESCRIPTION: SEQ ID NO: 52:

```
Leu Glu Thr Tyr Cys Ala Thr Pro
1               5
```

(2) INFORMATION FOR SEQ ID NO:    53:

(i) SEQUENCE CHARACTERISTICS:
        (A) LENGTH:           8
        (B) TYPE:             amino acid
        (C) STRANDEDNESS:
        (D) TOPOLOGY:         linear (xi) SEQUENCE DESCRIPTION: SEQ ID NO: 53:

```
Cys Ala Thr Pro Ala Lys Ser Glu
1               5
```

(2) INFORMATION FOR SEQ ID NO:    54:

(i) SEQUENCE CHARACTERISTICS:
        (A) LENGTH:           8
        (B) TYPE:             amino acid
        (C) STRANDEDNESS:
        (D) TOPOLOGY:         linear (xi) SEQUENCE DESCRIPTION: SEQ ID NO: 54:

```
Tyr Cys Ala Pro Ala Lys Ser Glu
1               5
```

(2) INFORMATION FOR SEQ ID NO:    55:

(i) SEQUENCE CHARACTERISTICS:
        (A) LENGTH:           5
        (B) TYPE:             amino acid
        (C) STRANDEDNESS:
        (D) TOPOLOGY:         linear (xi) SEQUENCE DESCRIPTION: SEQ ID NO: 55:

```
Tyr Cys Ala Pro Ala
1               5
```

(2) INFORMATION FOR SEQ ID NO:    56:

(i) SEQUENCE CHARACTERISTICS:
        (A) LENGTH:           6
        (B) TYPE:             amino acid
        (C) STRANDEDNESS:
        (D) TOPOLOGY:         linear (xi) SEQUENCE DESCRIPTION: SEQ ID NO: 56:

```
Thr Tyr Cys Ala Pro Ala
1               5
```

(2) INFORMATION FOR SEQ ID NO:    57:

(i) SEQUENCE CHARACTERISTICS:
        (A) LENGTH:           12
        (B) TYPE:             amino acid
        (C) STRANDEDNESS:
        (D) TOPOLOGY:         linear (xi) SEQUENCE DESCRIPTION: SEQ ID NO: 57:

```
Cys Thr Tyr Cys Ala Thr Pro Ala Lys Ser Glu Cys
1               5                   10
```

(2) INFORMATION FOR SEQ ID NO:    58:

(i) SEQUENCE CHARACTERISTICS:
        (A) LENGTH:           13
        (B) TYPE:             amino acid

```
        (C) STRANDEDNESS:
        (D) TOPOLOGY:           linear (xi) SEQUENCE DESCRIPTION: SEQ ID NO: 58:

Cys Glu Pro Tyr Cys Ala Pro Pro Ala Lys Ser Glu Cys
1               5                   10

(2) INFORMATION FOR SEQ ID NO:    59:

(i) SEQUENCE CHARACTERISTICS:
        (A) LENGTH:             11
        (B) TYPE:               amino acid
        (C) STRANDEDNESS:
        (D) TOPOLOGY:           linear (xi) SEQUENCE DESCRIPTION: SEQ ID NO: 59:

Cys Thr Tyr Cys Ala Pro Ala Lys Ser Glu Cys
1               5                   10

(2) INFORMATION FOR SEQ ID NO:    60:

(i) SEQUENCE CHARACTERISTICS:
        (A) LENGTH:             11
        (B) TYPE:               amino acid
        (C) STRANDEDNESS:
        (D) TOPOLOGY:           linear (xi) SEQUENCE DESCRIPTION: SEQ ID NO: 60:

Cys Thr Tyr Thr Ala Pro Ala Lys Ser Glu Cys
1               5                   10

(2) INFORMATION FOR SEQ ID NO:    61:

(i) SEQUENCE CHARACTERISTICS:
        (A) LENGTH:             15
        (B) TYPE:               amino acid
        (C) STRANDEDNESS:
        (D) TOPOLOGY:           linear (xi) SEQUENCE DESCRIPTION: SEQ ID NO: 61:

Cys Ala Leu Leu Glu Thr Tyr Ala Thr Pro Ala Lys Ser Glu Cys
1               5                   10                  15

(2) INFORMATION FOR SEQ ID NO:    62:

(i) SEQUENCE CHARACTERISTICS:
        (A) LENGTH:             18
        (B) TYPE:               amino acid
        (C) STRANDEDNESS:
        (D) TOPOLOGY:           linear (xi) SEQUENCE DESCRIPTION: SEQ ID NO: 62:

Cys Arg Arg Leu Glu Met Tyr Cys Ala Pro Leu Lys Pro Ala Lys Ser
1               5                   10                  15
Ala Cys (2) INFORMATION FOR SEQ ID NO:    63:

(i) SEQUENCE CHARACTERISTICS:
        (A) LENGTH:             14
        (B) TYPE:               amino acid
        (C) STRANDEDNESS:
        (D) TOPOLOGY:           linear (xi) SEQUENCE DESCRIPTION: SEQ ID NO: 63:

Cys Gly Tyr Gly Ser Ser Ser Arg Arg Ala Pro Gln Thr Cys
1               5                   10
```

(2) INFORMATION FOR SEQ ID NO:   64:

(i) SEQUENCE CHARACTERISTICS:
        (A) LENGTH:          11
        (B) TYPE:            amino acid
        (C) STRANDEDNESS:
        (D) TOPOLOGY:        linear (xi) SEQUENCE DESCRIPTION: SEQ ID NO: 64:

Cys Tyr Phe Asn Lys Pro Thr Gly Tyr Gly Cys
1               5                   10

(2) INFORMATION FOR SEQ ID NO:   65:

(i) SEQUENCE CHARACTERISTICS:
        (A) LENGTH:          20
        (B) TYPE:            amino acid
        (C) STRANDEDNESS:
        (D) TOPOLOGY:        linear (xi) SEQUENCE DESCRIPTION: SEQ ID NO: 65:

Cys Tyr Phe Asn Lys Pro Thr Gly Tyr Gly Ser Ser Ser Arg Arg Ala
1               5                   10                  15

Pro Gln Thr Cys
            20

(2) INFORMATION FOR SEQ ID NO:   66:

(i) SEQUENCE CHARACTERISTICS:
        (A) LENGTH:          12
        (B) TYPE:            amino acid
        (C) STRANDEDNESS:
        (D) TOPOLOGY:        linear (xi) SEQUENCE DESCRIPTION: SEQ ID NO: 66:

Cys Lys Pro Thr Gly Tyr Gly Ser Ser Ser Arg Cys
1               5                   10

(2) INFORMATION FOR SEQ ID NO:   67:

(i) SEQUENCE CHARACTERISTICS:
        (A) LENGTH:          16
        (B) TYPE:            amino acid
        (C) STRANDEDNESS:
        (D) TOPOLOGY:        linear (xi) SEQUENCE DESCRIPTION: SEQ ID NO: 67:

Arg Arg Leu Glu Met Tyr Cys Ala Pro Leu Lys Pro Ala Lys
1               5                   10

Ser Ala
15

(2) INFORMATION FOR SEQ ID NO:   68:

(i) SEQUENCE CHARACTERISTICS:
        (A) LENGTH:          10
        (B) TYPE:            amino acid
        (C) STRANDEDNESS:
        (D) TOPOLOGY:        linear (xi) SEQUENCE DESCRIPTION: SEQ ID NO: 68:

Thr Tyr Cys Ala Thr Pro Ala Lys Ser Glu
1               5                   10

(2) INFORMATION FOR SEQ ID NO:   69:

```
        (i) SEQUENCE CHARACTERISTICS:
            (A) LENGTH:              11
            (B) TYPE:                amino acid
            (C) STRANDEDNESS:
            (D) TOPOLOGY:            linear (xi) SEQUENCE DESCRIPTION: SEQ ID NO: 69:

Glu Pro Tyr Cys Ala Pro Pro Ala Lys Ser Glu
1               5                  10

(2) INFORMATION FOR SEQ ID NO:    70:

(i) SEQUENCE CHARACTERISTICS:
            (A) LENGTH:              9
            (B) TYPE:                amino acid
            (C) STRANDEDNESS:
            (D) TOPOLOGY:            linear (xi) SEQUENCE DESCRIPTION: SEQ ID NO: 70:

Thr Tyr Cys Ala Pro Ala Lys Ser Glu
1               5

(2) INFORMATION FOR SEQ ID NO:    71:

(i) SEQUENCE CHARACTERISTICS:
            (A) LENGTH:              14
            (B) TYPE:                amino acid
            (C) STRANDEDNESS:
            (D) TOPOLOGY:            linear (xi) SEQUENCE DESCRIPTION: SEQ ID NO: 71:

Ala Leu Leu Glu Thr Tyr Ser Ala Thr Pro Ala Lys Ser Glu
1               5                  10

(2) INFORMATION FOR SEQ ID NO:    72:

(i) SEQUENCE CHARACTERISTICS:
            (A) LENGTH:              11
            (B) TYPE:                amino acid
            (C) STRANDEDNESS:
            (D) TOPOLOGY:            linear (xi) SEQUENCE DESCRIPTION: SEQ ID NO: 72:

Glu Thr Gln Cys Ala Thr Pro Ala Lys Ser Glu
1               5                  10

(2) INFORMATION FOR SEQ ID NO:    73:

(i) SEQUENCE CHARACTERISTICS:
            (A) LENGTH:              24
            (B) TYPE:                amino acid
            (C) STRANDEDNESS:
            (D) TOPOLOGY:            linear (xi) SEQUENCE DESCRIPTION: SEQ ID NO: 73:

Gly Ala Glu Leu Val Asp Ala Leu Gln Phe Tyr Ser Gly Asp Arg Gly Phe
1               5                  10                  15
Tyr Phe Asn Lys Pro Thr Gly
            20

(2) INFORMATION FOR SEQ ID NO:    74:

(i) SEQUENCE CHARACTERISTICS:
            (A) LENGTH:              12
            (B) TYPE:                amino acid
            (C) STRANDEDNESS:
            (D) TOPOLOGY:            linear
```

(xi) SEQUENCE DESCRIPTION: SEQ ID NO: 74:

Ala Leu Leu Glu Thr Tyr Cys Ala Thr Pro Ala Lys
1               5                   10

(2) INFORMATION FOR SEQ ID NO:   75:

(i) SEQUENCE CHARACTERISTICS:
        (A) LENGTH:             10
        (B) TYPE:               amino acid
        (C) STRANDEDNESS:
        (D) TOPOLOGY:           linear (xi) SEQUENCE DESCRIPTION: SEQ ID NO: 75:

Leu Glu Thr Tyr Cys Ala Thr Pro Ala Lys
1               5                   10

(2) INFORMATION FOR SEQ ID NO:   76:

(i) SEQUENCE CHARACTERISTICS:
        (A) LENGTH:             14
        (B) TYPE:               amino acid
        (C) STRANDEDNESS:
        (D) TOPOLOGY:           linear (xi) SEQUENCE DESCRIPTION: SEQ ID NO: 76:

Ala Leu Leu Glu Thr Tyr Met Ala Thr Pro Ala Lys Ser Glu
1               5                   10

(2) INFORMATION FOR SEQ ID NO:   77:

(i) SEQUENCE CHARACTERISTICS:
        (A) LENGTH:             5
        (B) TYPE:               amino acid
        (C) STRANDEDNESS:
        (D) TOPOLOGY:           linear (xi) SEQUENCE DESCRIPTION: SEQ ID NO: 77:

Pro Ala Lys Ser Glu
1               5

(2) INFORMATION FOR SEQ ID NO:   78:

(i) SEQUENCE CHARACTERISTICS:
        (A) LENGTH:             9
        (B) TYPE:               amino acid
        (C) STRANDEDNESS:
        (D) TOPOLOGY:           linear (xi) SEQUENCE DESCRIPTION: SEQ ID NO: 78:

Thr Tyr Ser Ala Pro Ala Lys Ser Glu
1               5

(2) INFORMATION FOR SEQ ID NO:   79:

(i) SEQUENCE CHARACTERISTICS:
        (A) LENGTH:             11
        (B) TYPE:               amino acid
        (C) STRANDEDNESS:
        (D) TOPOLOGY:           linear (xi) SEQUENCE DESCRIPTION: SEQ ID NO: 79:

Glu Lys Tyr Cys Ala Lys Pro Ala Lys Ser Glu
1               5                   10

TREATING RETINAL NEURONAL DISORDERS BY THE APPLICATION OF INSULIN-LIKE GROWTH FACTORS AND ANALOGS

This application is a continuation-in-part of Bozyczko-Coyne et al. U.S. Ser. No. 07/790,690 filed on Nov. 8, 1991 now abandoned.

BACKGROUND OF THE INVENTION

The field of the invention is retinal neuronal disorders.

Insulin-like growth factors (IGFs) have been identified in various animal species as polypeptides that act to stimulate growth of cells in a variety of tissues (Baxter et al., 1988, Comp. Biochem. Physiol. 91B:229–235; Daughaday et al., 1989, Endocrine Rev. 10: 68–91), particularly during development (D'Ercole, 1987, J. Devel. Physiol. 9:481–495). The IGFS, each of which has a molecular weight of about 7,500 daltons, are chemically related to human proinsulin: i.e. they possess A and B domains that (1) are highly homologous to the corresponding domains of proinsulin, and (2) are connected by a smaller and unrelated C domain. A carboxyterminal extension, the D domain, is also present in IGFs but is not found in proinsulin. Functional homologies between the IGFs and insulin also exist. Like insulin, IGFs stimulate phosphorylation of specific tyrosine residues within the cytoplasmic domain of the receptors to which they bind.

Using peptide specific antibodies as probes, IGF-I and IGF-II (sometimes respectively termed "somatomedin C" and "somatomedin A" have been found in a variety of tissues, including the mammalian central nervous system (CNS); the presence of mRNAs encoding these polypeptides in the CNS suggests local synthesis in the CNS (Baskin et al., 1988, TINS 11:107–111). In addition, IGF-III [or "brain IGF", or IGF-I(4–70], a truncated form of IGF-I lacking the latter protein's three N-terminal amino acid residues, has been found in fetal and adult human brain (Sara et al., 1986, Proc. Natl. Acad. Sci. USA 83:4904–4907) as well as in colostrum (Francis et al., 1988, Biochem. J. 251:95–103).

IGF receptors have been isolated from peripheral tissues as well as from brain tissue (Waldbillig, R. J. et al., 1988, Exp. Eye Res. 47:587–607; Massague, J. and M. P. Czech. 1982, J. Biol. Chem. 257:5038–5045; Rechler, M. M. and S. P. Nissley, 1985, Ann. Rev. Physiol. 47:425–442). The receptors found in the cell membrane are either dimers, comprised of one alpha and one beta subunit, or heterotetramers, comprised of two alpha/beta subunit pairs. Although IGFs bind to the dimeric form of the receptor, functional activation occurs only upon binding to the heterotetrameric species (Tollefsen, S. E. et al., 1991, Biochemistry. 30:48–54). IGF receptors isolated from peripheral and brain tissue differ in the molecular weights of their alpha subunits (Waldbillig, R. J. et al., 1988, Exp. Eye Res. 47:587–607), and even within brain tissue, IGF receptors isolated from neuronal cells are different to those isolated from glial cells (Burgess, S. K. et al., 1987, J. Biol. Chem. 262:1618–1622). Whether these differences reflect altered functional or binding specificities is not known. Finally, European Patent Application No. 86850417.6 describes evidence for a another type of IGF receptor located in human fetal membranes.

IGF-I and IGF-II appear to exert a stimulatory effect on development or proliferation of a wide range of susceptible cell types (Daughaday et al., Supra). Treatment with IGFs, or with certain polypeptide fragments thereof, has been variously suggested as a bone repair and replacement therapy (European Patent Application No. 88303855.6), as a means to counteract certain harmful side effects of carcinostatic drugs (Japanese Patent Application No. 63196524), and as a way to increase lactation and meat production in cattle and other farm animals (Larsen et al., U.S. Pat. No. 4,783,524). The effects of IGF on cells obtained from various parts of the CNS, and from the peripheral nervous system has been studied (Aizenman et al., 1987, Brain Res. 406:32–42; Fellows et al., 1987, Soc. Neurosci. Abstr. 13:1615; Onifer et al., 1987, Soc. Neurosci. Abstr. 13:1615; European Patent Application No. 86850417.6; Bothwell 1982, J. Neurosci. Res. 8:225–231; Recio-Pinto et al., 1986, J. Neurosci. 6:1211–1219). In addition, the IGFs have been shown to affect the development of undifferentiated neuronal-like cells: When IGFs were added to the growth medium of human neuroblastoma tumor cells, these cells were observed to extend neurites and to undergo mitosis (Recio-Pinto and Ishii, 1988, J. Neurosci. Res. 19:312–320; Mattson et al., 1986, J. Cell Biol. 102:1949–1954).

Within nervous tissue, IGFs have been shown to induce glial cell enzyme activities (McMorris et al., 1985, J. Neurochem. 44:1242–1251), to induce differentiation and development of oligodendrocytes (McMorris and Dubois-Dalcq, 1988, Neurosci. Res. 21:199–209), and to support embryonic brain cell proliferation, development and neurite outgrowth (Neilsen, F. and S. Gammeltoft, 1990, FEBS Letters 262:142–144; Svrzic and Schubert, 1990, Biochem. Biophys. Res. Comm. 172:54–60; Torres-Alwman, et al., 1990, Neuroscience 35:601–608; Recio-Pinto et al., 1986, J. Neurosci. 6:1211–1219).

IGFs have been found in both the developing and adult eye in the aqueous (Tripathi et al., 1991, Dev. Drug Res. 22:1–23) and vitreous humor (Grant et al., 1991, Diabetes 35:416–420). Autoradiographic studies using iodinated peptides revealed IGF binding sites within the uveal tract, choroid, lens, sclera and retina (Bassas, et al., 1989, Endocrinology 125:1255–2320; Bassnett and Beebe, 1990, Invest. Ophthalmol. Vis. Sci. 31:1637–1643; Waldbillig, et al., 1990, Invest. Ophthalmol. Vis. Sci. 31:1015–1022). In the adult retina, IGF-I binding sites appear to be specifically localized to the nuclear layers, and the photoreceptor regions, including the rod outer segments (Ocrant, et al., 1989, Endocrinology 125:2407–2413; Waldbillig, et al., 1988, Exp. Eye. Res. 47:587–607; Zick et al., 1987, J. Biol. Chem. 262:10259–10264), whereas proteins immunologically related to IGF-II receptors have been demonstrated in the retinal pigment epithelium (Ocrant et al., 1989, Endocrinology 125:2407–2413). IGF-I and IGF-II MRNA levels are highest within the retina of the eye (Danias and Stylianopoulou 1990, Curr. Eye Res. 9:379–386). However, the function of IGFs in the eye is unknown and the IGF binding sites in the retina have not been fully characterized. Therefore, it is not yet known whether these sites actually function as IGF receptors, i.e. whether they mediate a biological response.

It has been speculated, based upon results establishing that IGF-I affects the permeability of membranes for potassium (Beebe et al., 1986, Prog. Dev. Biol. Part A: 365–369; Parmelee and Beebe, 1988, J. Cell Phys. 134; 491–496) and that outer and inner rod segments contain IGF binding sites (Waldbillig et al., 1988, Exp. Eye. Res. 47:587–607; Zick et al., 1987, J. Biol. Chem. 262:10259–10264), that IGF-I might be involved in light transduction.

With regard to diabetic retinopathy, where the major pathological finding in the eye is neovascularization, King et al. (1985, J. Clin. Invest. 75:1028–1036) state that "In the present study, we have characterized the receptors and the growth promoting effect of insulin-like growth factor (IGF-I) and multiplication-stimulating activity (MSA, and IGF-II) on endothelial cells and pericytes from calf retinal capillaries and on endothelial and smooth muscle cells from calf aorta.," and, "These data show that vascular cells have insulin and IGF receptors but have a differential response to these hormones. These differences in biological response between cells from retinal capillaries and large arteries could provide clues to understanding the pathogenesis of diabetic micro-and macroangiopathy". In addition, Grant et al. (1986, Diabetes 35:416–420) state that "The concentrations of IGF-I in the vitreous of most diabetic subjects with severe neovascularization are thus in the range known to stimulate cellular differentiation and growth in several systems. Whether they do so in the eye, and thus contribute to the development of retinopathy, remains to be determined".

SUMMARY OF THE INVENTION

In one aspect, the invention features a method of enhancing the survival of retinal neuronal cells at risk of dying in a mammal, by administering to the mammal an effective dose of at least one of the following substances: IGF-I; a functional derivative of IGF-I; IGF-II; or a functional derivative of IGF-II.

In preferred embodiments, where there is administered IGF-I, IGF-II, or a functional derivative of IGF-I or IGF-II, the method further comprises administering to the mammal an effective amount of a substance which produces an additive and/or synergistic effect. A combination of two or more of the substances, which act synergistically, can be administered to the mammal, or a combination of two or more of the substances, which act additively, can be administered to the mammal.

In other preferred embodiments, the retinal neuronal cells are photoreceptor cells, amacrine cells, horizontal cells, bipolar cells, or ganglion cells.

In yet other preferred embodiments, the method is used in a therapeutic context for the treatment of retinal neuronal tissues which are suffering from the effects of injury, aging and/or disease, wherein the term injury is a broad term which includes, but is not limited to, injury resulting in retinal degeneration, such as photodegeneration, trauma, axotomy, neurotoxic-excitatory degeneration or ischemic neuronal degeneration, and wherein the term disease is a broad term which includes, but is not limited to, any infectious or non-infectious disease such as inherited retinal dystrophy, diabetic retinopathy, Alzheimer's disease, infantile malignant osteopetrosis, ceroid-lipofuscosis or cholestasis.

In preferred embodiments, wherein a functional derivative of IGF-I is administered, IGF-I(4–70) (SEQ ID NO:2), also known as IGF-III or brain IGF, is the preferred IGF-I derivative. Where a functional derivative of IGF-II is administered, IGF-II(54–67) (SEQ ID NO:13) is the preferred IGF-II derivative. The substances can also be administered in conjunction with neurotransmitter enhancers and/or their derivatives.

IGF-I, IGF-II, or functional derivatives thereof administered in methods of the invention may be chemically modified in such a way as to increase its efficacy, e.g., by increasing the transport of these polypeptides across the blood-retina barrier, e.g., by modifications of the polypeptide that increase lipophilicity, alter glycosylation, or increase net positive charge.

The invention also features a composition comprising a solution containing IGF-I or IGF-II, or a functional derivative thereof, e.g., IGF-I(4–70) (SEQ ID NO:2), or IGF-II (54–67) (SEQ ID NO:13), with excipients for ophthalmic administration, contained within a chemically inert vessel which is closed at one end with a dropper or other device for the transfer of drops of the solution from the vessel to the eye of the recipient of the solution. The invention also features a composition comprising a solution containing IGF-I or IGF-II, or a functional derivative thereof, e.g., IGF-I(4–70) (SEQ ID NO:2), or IGF-II (54–67) (SEQ ID NO:13), with excipients for ophthalmic administration, contained within a chemically inert vessel, e.g., an implant, e.g., an implanted disk, which is implanted into a recipient for the transfer of the solution from the implant to the eye of the recipient.

The invention features a composition comprising an ointment containing IGF-I or IGF-II, or a functional derivative thereof, e.g., IGF-I(4–70) (SEQ ID NO:2), or IGF-II (54–67) (SEQ ID NO:13), with excipients for ophthalmic administration.

As a preferred embodiment to the method of the invention, the functional derivative is a substantially pure peptide comprising a sequence selected from the group consisting of the amino acid sequence CALLETYCATPAKSEC (SEQ ID NO:17, the amino acid sequence CTYCATPAKSEC (SEQ ID NO:57), the amino acid sequence CEPYCAPPAKSEC (SEQ ID NO:58), and the amino acid sequence CTYCAPAKSEC (SEQ ID NO:59), wherein the N-terminal cysteine is connected to the C-terminal cysteine by a covalent bond.

As a preferred embodiment to the method of the invention the functional derivative is a substantially pure peptide comprising a sequence selected from the group consisting of the amino acid sequence CALLETDYCATPAKSEC (SEQ ID NO:47), the amino acid sequence CTDYCATPAKSEC (SEQ ID NO:48), and the amino acid sequence CTDYCAPAKSEC (SEQ ID NO:49), wherein the N-terminal cysteine is connected to the C-terminal cysteine by a covalent bond.

As a preferred embodiment to the method of the invention the functional derivative is a substantially pure peptide comprising a sequence selected from the group consisting of the amino acid sequence CTYTAPAKSEC (SEQ ID NO:60), the amino acid sequence CALLETYATPAKSEC (SEQ ID NO:61), the amino acid sequence CRRLEMYCAPLKPAKSAC (SEQ ID NO:62), the amino acid sequence CGYGSSSRRAPQTC (SEQ ID NO:63), the amino acid sequence CYFNKPTGYGC (SEQ ID NO:64), the amino acid sequence CYFNKPTGYGSSSRRAPQTC (SEQ ID NO:65), and the amino acid sequence CKPTGYGSSSRC (SEQ ID NO:66), wherein the N-terminal cysteine is connected to the C-terminal cysteine by a covalent bond.

As a preferred embodiment to the method of the invention, the functional derivative is a substantially pure peptide selected from the group consisting of the amino acid sequence CDLRRLEMYC (SEQ ID NO:19), the amino acid sequence CCFRSCDLRRLEMYC (SEQ ID NO:20), the amino acid sequence CCFRSC (SEQ ID NO:22), and the amino acid sequence CFRSC (SEQ ID NO:23), wherein said peptide is cyclized by a covalent bond between two residues of said peptide.

As a preferred embodiment to the method of the invention the functional derivative is a substantially pure peptide selected from the group consisting of the amino acid sequence TYCATPAKSE (SEQ ID NO:68), and the amino acid sequence RRLEMYCAPLKPAKSA (SEQ ID NO:67). The residues flanking the amino acid sequence can be homologous to the naturally occurring sequence of IGF-I, or to the naturally occurring sequence of IGF-II.

As a preferred embodiment to the method of the invention, the functional derivative is a substantially pure cyclized peptide consisting essentially of the amino acid sequences CGCELVDALQFVC (SEQ ID NO:18) and CCFRSCDLRRLEMYC (SEQ ID NO:20), wherein said cyclized peptide comprises at least one covalent bond between two residues of said cyclized peptide.

As a preferred embodiment to the method of the invention, the functional derivative is a substantially pure peptide comprising a sequence selected from the group consisting of the amino acid sequence CGCELVDALQFVC (SEQ ID NO:18), the amino acid sequence CDLRRLEMYCCPLKPAKSE (SEQ ID NO:21), the amino acid sequence CGPETLC (SEQ ID NO:26), the amino acid sequence CGYGSSSRRCPQTGIVDEC (SEQ ID NO:27), the amino acid sequence CGDRGFYFNKPTC (SEQ ID NO:28), the amino acid sequence CCPLKPAKSAC (SEQ ID NO:29), and the amino acid sequence CDLRRLEMYAPLKPAKSAC (SEQ ID NO:30), wherein the N-terminal cysteine is connected to the C-terminal cysteine by a covalent bond.

As a preferred embodiment to the method of the invention, the functional derivative is a substantially pure peptide selected from the group consisting of the amino acid sequence CGGELVDTLQFVC (SEQ ID NO:32), the amino acid sequence CCFRSCDDLALLETYC (SEQ ID NO:34), wherein said peptide is cyclized by a covalent bond between two residues of said peptide. Preferably, the residues flanking the amino acid sequence are homologous to the naturally occurring sequence of IGF-I, or to the naturally occurring sequence of IGF-II.

As a preferred embodiment to the method of the invention, the functional derivative is a substantially pure cyclized peptide consisting essentially of the amino acid sequences CGGELVDTLQFVC (SEQ ID NO:32) and CCFRSCDLCLLETYC (SEQ ID NO:39), wherein said cyclized peptide comprises at least one covalent bond between two residues of said cyclized peptide.

As a preferred embodiment to the method of the invention, the functional derivative is a substantially pure peptide comprising a sequence selected from the group consisting of the amino acid sequence CDLCLLETYC (SEQ ID NO:33), the amino acid sequence CDLCLLETYCATPAKSE (SEQ ID NO:35), the amino acid sequence CCYRPSETLC (SEQ ID NO:40), CRPCSRVSRRSRGIVEEC (SEQ ID NO:41), CGDRGFYFSRPC (SEQ ID NO:42), CCTPAKSEC (SEQ ID NO:43), and CDLCLLETATPAKSEC (SEQ ID NO:44), wherein the N-terminal cysteine is connected to the C-terminal cysteine by a covalent bond.

As a preferred embodiment to the method of the invention, the functional derivative is a substantially pure peptide comprising a sequence selected from the group consisting of the amino acid sequence CATPAKSE (SEQ ID NO:53), YCAPAKSE (SEQ ID NO:54), YCAPA (SEQ ID NO:55), TYCAPA (SEQ ID NO:56), CAPAKSE (SEQ ID NO:24), EALLETYCATPAKSE (SEQ ID NO:36), and APSTCEYKA (SEQ ID NO:38).

As a preferred embodiment to the method of the invention the functional derivative is a substantially pure peptide selected from the group consisting of the amino acid sequence YFNKPTGYGSSSRRAPQT (SEQ ID NO:3), the amino acid sequence GYGSSSRRAPQT (SEQ ID NO:4), the amino acid sequence APLKPAKSA (SEQ ID NO:5), the amino acid sequence YFNKPTGYG (SEQ ID NO:6), the amino acid sequence SSSRRAPQT (SEQ ID NO:10), the amino acid sequence PTGYGSSSRRAPQT (SEQ ID NO:11), and the amino acid sequence KPTGYGSSSR (SEQ ID NO:12). Preferably, the residues flanking the amino acid sequence are homologous to the naturally occurring sequence of IGF-I, or to the naturally occurring sequence of IGF-II.

As a preferred embodiment to the method of the invention, the functional derivative is a substantially pure peptide comprising a sequence selected from the group consisting of the amino acid sequence YFNKPTGYGSSSRRAPQT-NH$_2$ (SEQ ID NO:7), the amino acid sequence SSSRRAPQT-NH$_2$, the amino acid sequence GIVDECC(Acm)FRSCLDRRL-NH$_2$ (SEQ ID NO:9), the amino acid sequence EPYCAPPAKSE (SEQ ID NO:69), the amino acid sequence TYCAPAKSE (SEQ ID NO:70), the amino acid sequence ALLETYSATPAKSE (SEQ ID NO:71), the amino acid sequence ETQCATPAKSE (SEQ ID NO:72), and the amino acid sequence GAELVDALQFYSGDRGFYFNKPTG (SEQ ID NO:73).

As a preferred embodiment to the method of the invention, the functional derivative is a substantially pure peptide comprising a sequence selected from the group consisting of the amino acid sequence ALLETDYCATPAKSE (SEQ ID NO:45), the amino acid sequence TDYCATPAKSE (SEQ ID NO:46), and the amino acid sequence TDYCAPAKSE (SEQ ID NO:50).

As a preferred embodiment to the method of the invention, the functional derivative is a substantially pure peptide selected from the group consisting of the amino acid sequence ALLETYCATPAKSE (SEQ ID NO:13), the amino acid sequence TPAKSE (SEQ ID NO:14), and the amino acid sequence SRVSRRSR (SEQ ID NO:15).

As a additional embodiment, the functional derivative contains between 5 and 40 amino acids, preferably 6–25 amino acids. The functional derivative can be iodinated.

The functional derivative can also be a cyclic peptide, the cyclic peptide consisting essentially of 5–40 amino acid residues, or 6–25 amino acid residues. Preferably the cyclic peptide includes a fragment of the respective IGF-I, IGF-II, or IGF-III as at least a portion of its amino acid sequence. The cyclic peptide can include a disulfide bond between two cysteines of the peptide, the cysteines being located at either terminal or internal positions of the peptide. Alternatively or in addition to the disulfide bond, the cyclic peptide may include an amide bond between the amino and carboxyl ends of the peptide. Preferred cyclic peptides include, but are not limited to, those derived by cyclization, e.g., by disulfide bond formation or by amide bond formation.

As a preferred embodiment to the method of the invention, the functional derivative is a retro-inverso peptide, preferably a retro-inverso peptide that is homologous to IGF-I, or a fragment thereof, or a retro-inverso peptide that is homologous to IGF-II, or a fragment thereof. A "retro-inverso peptide", as used herein, refers to a peptide with a reversal of the direction of the peptide bond at at least one position, i.e., a reversal of the amino- and carboxy-termini with respect to the side chain of the amino acid. Retro-inverso peptides may contain L-amino acids or D-amino acids, or a mixture of L-amino acids and D-amino acids.

The functional derivative can also be a scrambled peptide. A "scrambled peptide", as used herein, is a peptide that contains the same residues of the naturally occurring peptide or a functional derivative thereof, but where the sequence of the residues has been rearranged.

With respect to any of the IGF-I or IGF-II peptides listed herein, most preferred are linear and cyclic peptides that contain at least one cysteine residue that is not involved in disulphide bond formation. In some cases where a naturally-occurring alanine has been changed to a cysteine, the invention embodies both the peptide containing the naturally-occurring alanine, which has at least partial activity, as well as the peptide containing the substituted cysteine, which has the preferred activity.

"Homologous" refers to the sequence similarity between two polypeptide molecules or between two nucleic acid molecules. When a position in both of the two compared sequences is occupied by the same base or amino acid monomeric subunit, e.g., if a position in each of two polypeptide molecules is occupied by leucine, then the molecules are homologous at that position. The homology between two sequences is a function of the number of matching or homologous positions shared by the two sequences. For example, 6 of 10, of the positions in two sequences are matched or homologous then the two sequences are 60% homologous. By way of example, the amino acid sequences Leu-gly-val-ala-gly-pro and Leu-his-tyr-ala-gly-leu share 50% homology.

In addition to substantially full-length polypeptides, the invention also includes fragments of the IGF-I, IGF-II, or IGF-III polypeptides. As used herein, the term "fragment", as applied to a polypeptide, will ordinarily be at least about 5 contiguous amino acids, typically at least about 20 contiguous amino acids, usually at least about 40 contiguous amino acids, and preferably at least about 60 or more contiguous amino acids in length. Fragments of IGF I, II, or III can be generated by methods known to those skilled in the art.

In a final aspect, the invention includes a substantially pure peptide, the peptide comprising a sequence selected from the group consisting of the amino acid sequence ALLETYSATPAKSE (SEQ ID NO:71), the amino acid sequence ETQCATPAKSE (SEQ ID NO:72), and the amino acid sequence GAELVDALQFYSGDRGFYFNKPTG (SEQ ID NO:73). Any of the peptides of the invention may be iodinated.

The peptides described herein are provided as examples, and are not to be construed as limiting the range of peptides useful for the methods of the invention.

Survival of treated retinal neuronal cells denotes maintenance of the cell's viability to an extent greater than that of untreated controls. Since the preponderance of retinal neuronal cells are commonly believed to be incapable of cell division, the ability of an agent to promote survival of such cells may be measured by assays which reproducibly indicate relative numbers of cells, such as directly counting cells which stain as viable cells, or which possess other characteristics of viable neurons. The method and composition of the invention are useful for therapeutically treating a disorder of a human or other mammal characterized by death and/or dysfunction of retinal neuronal cells, including disorders attributable to a disease of aging of, or injury to, such retinal neuronal cells.

Other features and advantages of the invention will be apparent from the following description of the preferred embodiments thereof, and from the claims.

DETAILED DESCRIPTION

The drawings are first described.

THE DRAWINGS

Figure 5A:
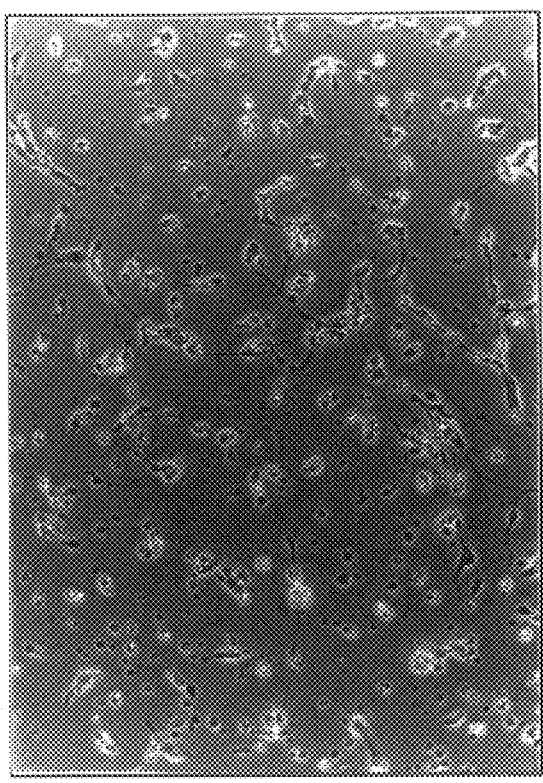
Figure 5B:

FIG. 5 contains photomicrographs illustrating the axonal regenerative effect of IGF-I on cultures of retinal neurons.

Figure 6:
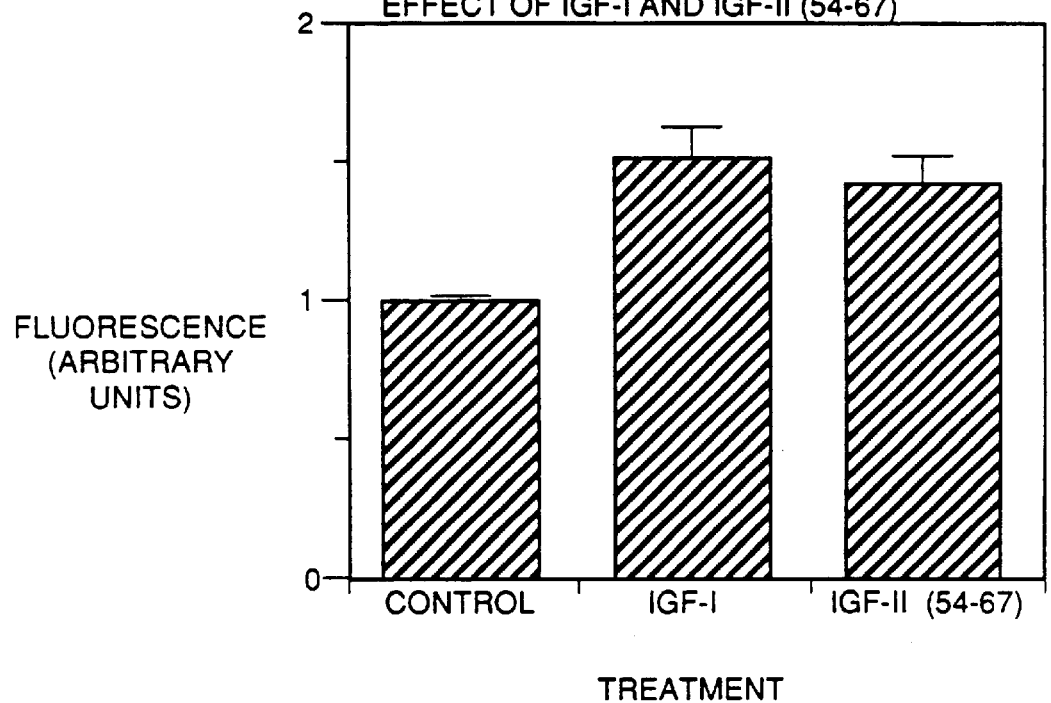

FIG. 6 is a histogram illustrating the effect of IGF-I and a peptide fragment of IGF-II (amino acids 54–67) on the survival of populations of retinal neurons.

Figures 7A, 7B:
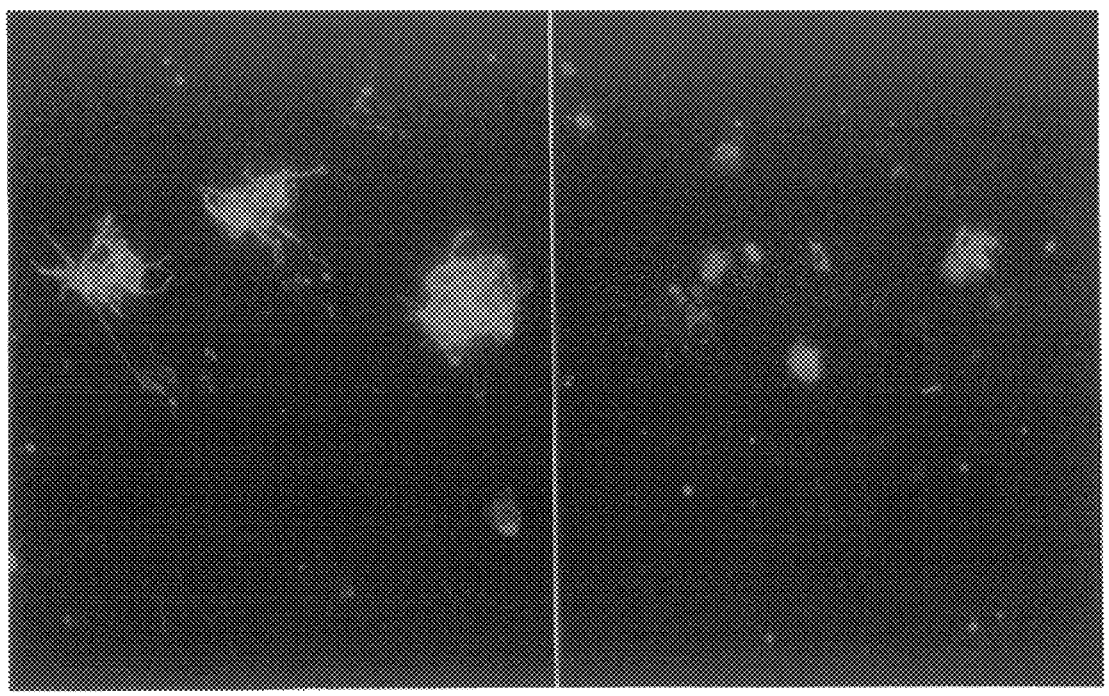

FIG. 7 contains photographs of IGF-I treated or untreated postnatal rat retinal neuronal cultures stained with Rho42 antibody.

Figure 8A:
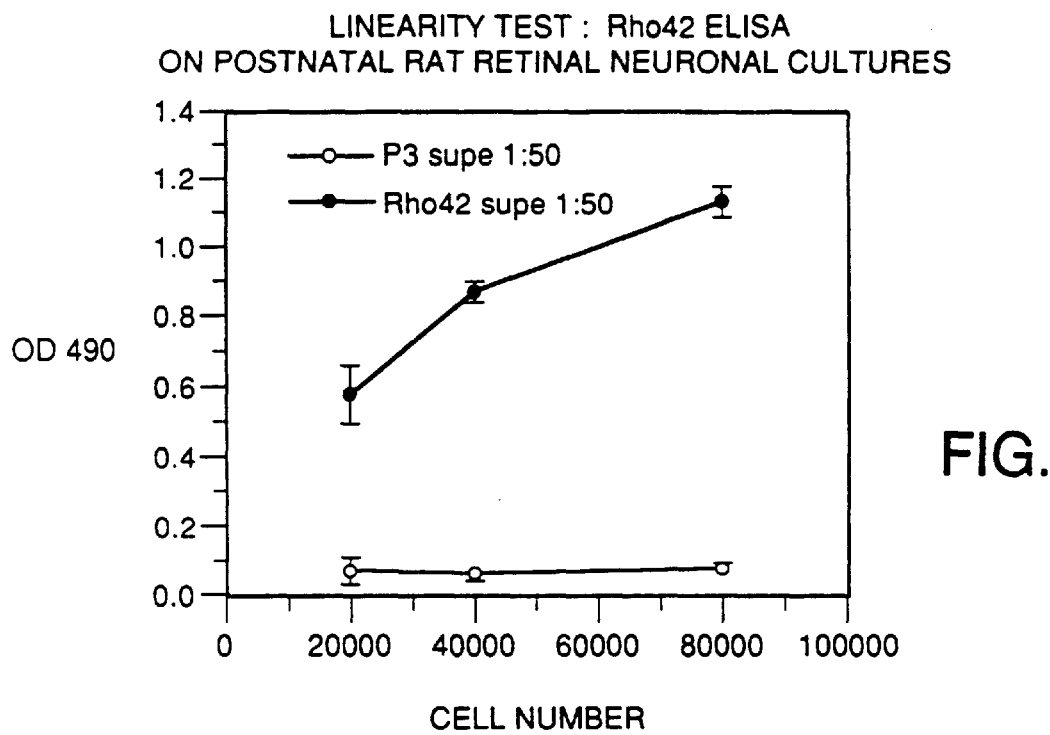
Figure 8B:
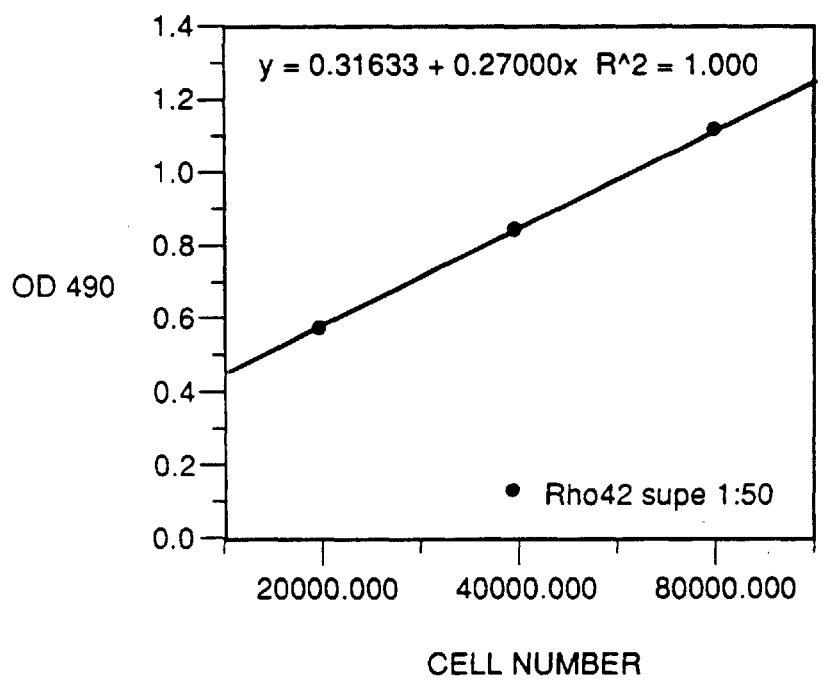

FIG. 8 contains two graphs which demonstrate the linearity of a cell-based Rho42 ELISA.

Figure 9:
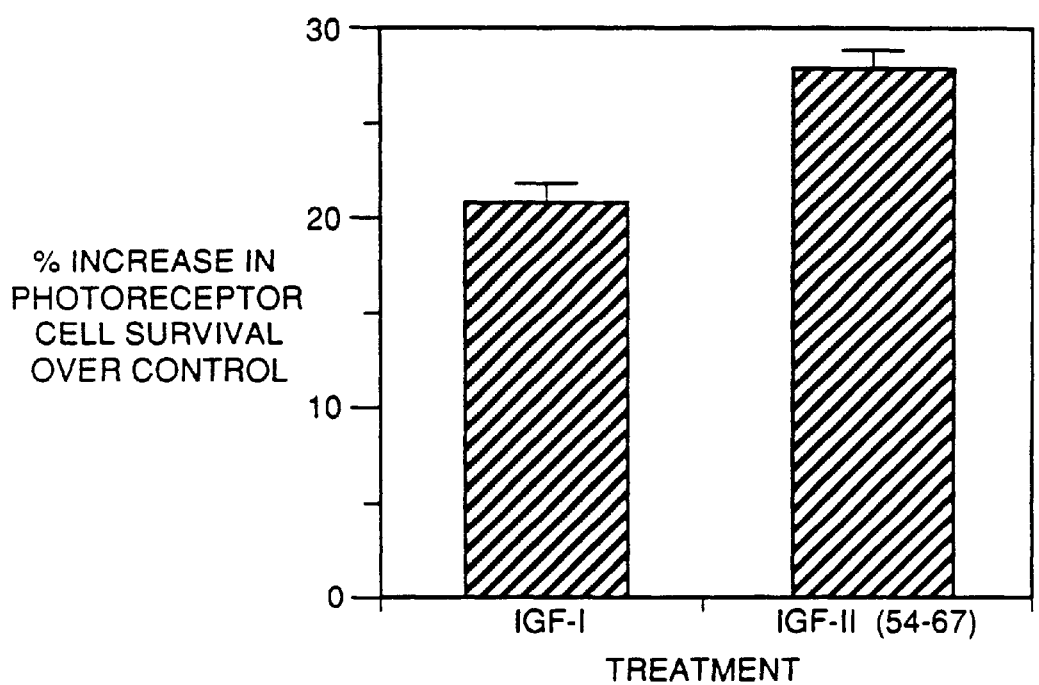

FIG. 9 is a histogram illustrating the effect of IGF-I and IGF-II (54–67) on the photoreceptor subpopulation of rat retinal neuronal cultures.

Figure 10:
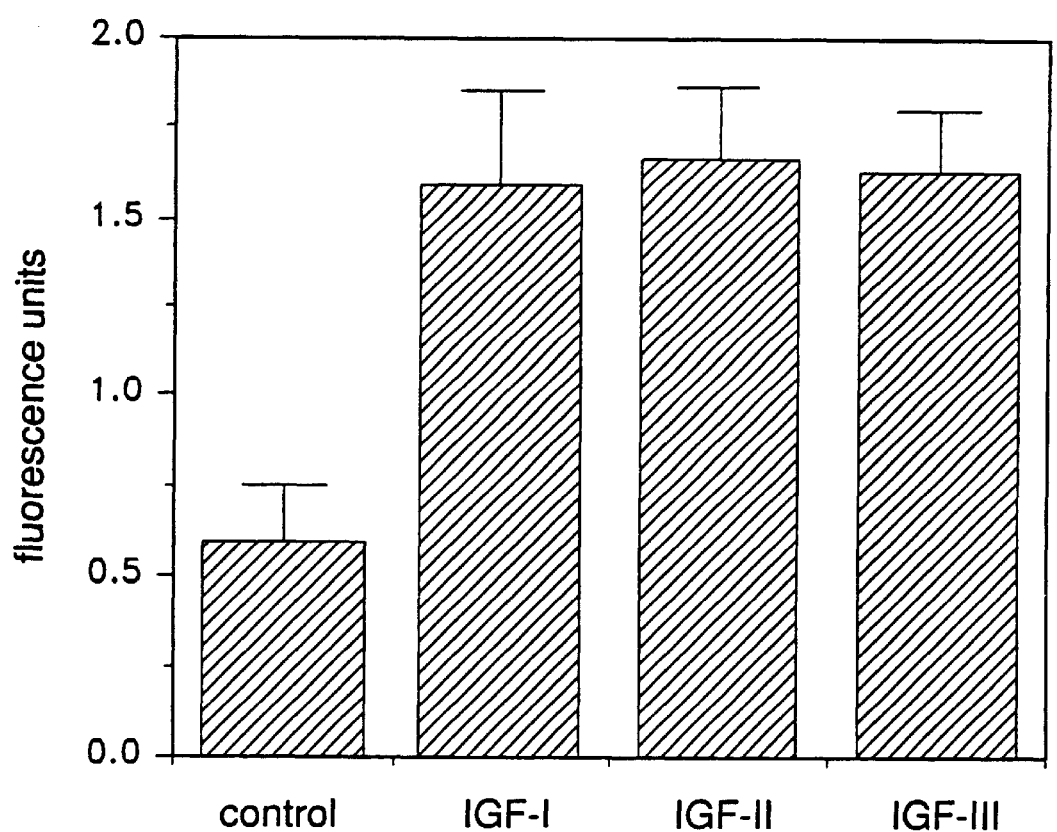

FIG. 10 is a graph showing the effect of IGF-I, IGF-II, and IGF-III on retinal neuronal cell survival.

Figure 11:
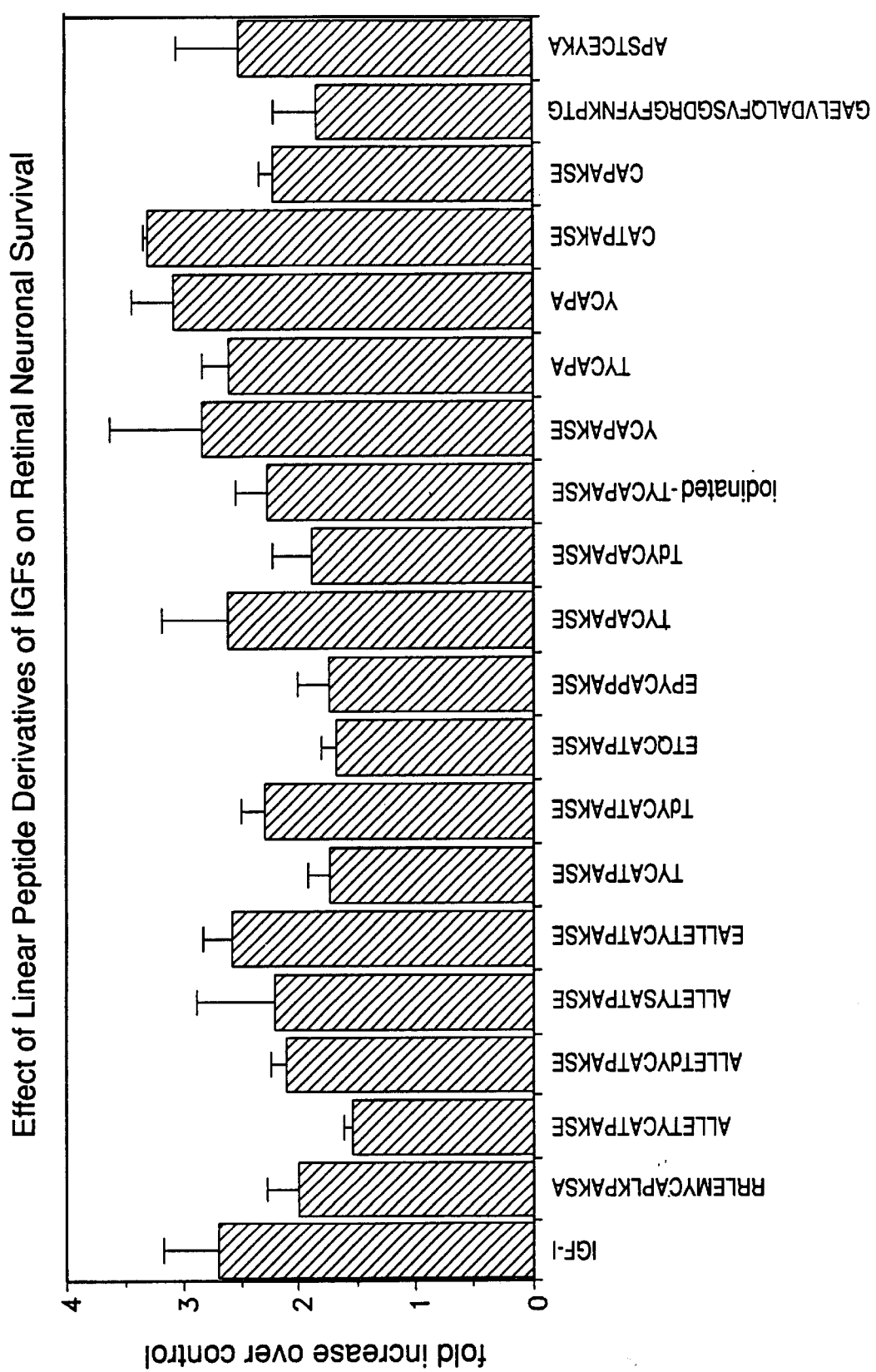

FIG. 11 is a graph showing the effect of linear peptide derivative on IGFs on retinal neuronal survival.

IGF-I, IGF-II and the Eye

We have discovered that IGFs function to promote the survival of cells prepared from dissociated retina obtained from both prenatal and postnatal retinal neuronal tissue. This finding is significant and unexpected in that other growth factors have not been demonstrated to promote survival of broad classes of retinal neuronal cells, both pre- and postnatally.

The Peptides

A "functional derivative" of a polypeptide is a compound which is a fragment or an analog of that molecule and which possesses the desired biological activity, herein defined as the ability to promote survival of retinal neuronal cells. A "fragment" of a polypeptide refers to any polypeptide subset of that polypeptide. An "analog" of a polypeptide refers to a molecule having biological activity but possessing some structural differences compared to the polypeptide. The analog preferably contains greater than or equal to 50% homology with the parent molecule and more preferably contains greater than or equal to 75% homology with the parent molecule. Analogs of polypeptides may contain altered amino acid sequences, or the presence of additional chemical moieties not normally a part of the molecule. Such moieties (introduced for example, by acylation, alkylation, cationization, or glycosylation reactions) may improve the molecule's solubility, adsorption, transport, biological half-life etc. Alternatively, or in addition, some moieties may decrease the toxicity of the molecule, or eliminate or attenuate any undesirable side effect of the molecule. Moieties capable of mediating such effects are disclosed in *Remington's Pharmaceutical Sciences* (Mack Pub. co., Easton, Pa., 1980). Although some derivatives of IGF-I and IGF-II may be inoperative alone or in combination, a person skilled in the art disclosed herein can recognize which are operative and which are not, as will be explained in more detail below.

Some of the compounds within the scope of this invention are depicted in Table 1, in which the amino acid sequences (expressed using single letter abbreviations as defined in Table 2) of IGF-I, IGF-II and a number of functional derivatives of IGF-I and IGF-II, are listed. The list in Table 1 is provided as an example, and the invention is not limited to the derivatives present therein. These derivatives were selected for study on the basis of one or more of the following criteria, which are related to the ability to bind to IGF-I or IGF-II receptors, and thus are useful for identifying additional derivatives of the invention: (1) conservation of amino acid sequence among species; (2) presence of "conservative" amino acid substitutions among species (i.e., amino acids with similar shape, charge or other salient characteristics); (3) receptor-shielding of tyrosine residues from radioiodination (Maly and Luthi, 1988, J. Biol. Chem. 263:7068); (4) predominance of hydrophilic residues, suggesting the location of a receptor-binding domain on the surface of the polypeptide, a presumptive requirement for receptor interaction; and (5) consideration of hydrophobic and polar regions of three-dimensional models (e.g., Blundell et al., 1983, Fed. Proc. 42:2592–2597) and identifying therefrom regions which are possible binding sites.

Since the bioavailability of peptides may be related to their lipophilicity or their net ionic charge, suitable modifications of these peptides, e.g., by substituting pentafluorophenylalanine for phenylalanine, or by conjugation to cationized albumin (Kastin et al., 1979, Biochem. Behav. 11:713–716; Rapoport et al., 1980, Science 207:84–86; Pardridge et al., 1987, Biochem. Biophys. Res. Commun. 146:307–313; Riekkinen et al., 1987, Peptides 8:261–265) may be important for their bioavailability, and these modifications are within the scope of the invention. In addition, since bioavailability of peptides may be limited by their susceptibility to degradation by proteases and peptidases (Littlewood et al., 1988, Neurochem. Int. 12:383–389), modifications of these peptides, e.g., replacement of L-amino acids with D-amino acids to increase their metabolic stability may also be important for their therapeutic efficacy, and these modified peptides are also within the scope of the invention.

Functional derivatives of the invention include, among others, peptides which vary from the native IGF molecules in any one or more of the following ways:

1. Chemical modification of the amino and carboxy groups present at the respective ends of the peptides.

2. Replacement of one or more of the amino acid residues in the native sequence with biologically compatible other amino acid residues.

3. Replacement of one or more of the amino acid residues in the native sequence with chemically modified, biologically compatible other amino acid residues.

4. Deletion of one or more of the amino acid residues in the native sequence.

5. Repetition of one or preferably a sequence of several amino acid residues in the native sequence, with or without chemical modification to, or replacement or deletion of, one or more members of the sequence.

6. Cyclization, that is, joining the amino acid and carboxy ends of the linear peptide.

7. Linkage of an IGF-I or IGF-II, or functional derivatives of either IGF-I or IGF-II with another molecule such as a polypeptide (e.g., another fragment of IGF-I or IGF-II) or a carbohydrate, by means of a disulfide, peptide, ester or other covalent bond.

8. Retro-inverso peptides.

9. "Scrambled" peptides.

The invention also utilizes as a preferred subgroup within the IGF functional derivatives having the sequence: $R_1$-$AA_1$-$AA_2$-$AA_3$-$AA_4$. . . $AA_n$-$R_2$, wherein $AA_1$, $AA_2$, $AA_3$, $AA_4$ . . . $AA_n$ are amino acid residues of IGF or of the IGF subsets or are conservative replacements for them as defined in Table 2, and n is any integer from 5 to 70 for IGF-I functional derivatives and 5–67 for IGF-II functional derivatives. $R_1$ is attached to the amino group of $AA_1$ and selected form the group of hydrogen, lower ($C_{1-6}$) alkyl, lower alkyl carbonyl, lower alkenyl, lower alkynyl, formyl, lower ($C_{6-10}$) aryl, aroyl, aryloxy-carbonyl, aralkyloxy-carbonyl, lower alkyloxycarbonyl, benzoyl, 1- or 2-thenoyl, nicotinoyl, dihydronicotinoyl, N-alkydihydroisonicotinoyl, isonicotinoyl, and N-alkyldihydroisonicotinoyl. The carboxy-terminal substituent ($R_2$) of the peptides is selected from the following: OH; $NH_2$, $OR_3$, wherein $R_3$ is a lower alkyl or a lower aryl; $OR_3OH$, wherein $R_3$ is defined as above; and NH—$R_3$ or N($CH_3$)$R_3$, wherein $R_3$ is defined as above. Alternatively, the carboxyl group of the carboxyl-terminal amino acid may be replaced by any one of —$PO_3H_2$, —$B(OH)_2$, —$CH_2OH$, —$SO_3H$ or a 5-tetrazole group.

The amino terminal amino group and/or the lysine, serine or threonine side chains occurring within the peptide may optionally be acylated by formyl, acetyl, propionyl, and similar lower alkylacyl residues or by aryl, or heterocyclic acyl residues such as benzoyl, thenoyl, nicotinoyl, isonicotinoyl, N-alkylnicotinoyl and their dihydro and tetrahydro derivatives. Such modifications would be expected to enhance the blood-brain barrier permeability of the therapeutic agent (Creveling et al., 1969, Experientia 25:26–27; Bodor et al., 1981, Science 214:1370–1372).

In peptide sequences containing proline, glutamic acid, or aspartic acid at the amino terminus, the amino terminal amino acid may optionally be replaced by L-pyroglutamic acid.

The fragment polypeptides of IGF-I or IGF-II are subsets of the IGF-I or IGF-II molecules respectively, containing fewer amino acid residues than the native molecules. A portion of the amino acids of the fragments may be substituted with conservative replacements or deletions which improve the chemical or biological stability of the product polypeptides or improve their transport across the blood-brain barrier. Preferably, no more than 30% and more preferably no more than 20% of the amino acid residues are replaced or deleted. A listing of suitable conservative replacements is given in Table 2, along with a key to the single-letter abbreviations for the common, naturally occurring amino acid residues found in proteins. Certain other abbreviations used in Table 2 are herein defined: by Nle is meant norleucine, by Aib is meant aminoisobutyric acid, by AdaA is meant β-adamantylalanine, by AdaG is meant α-adamantylglycine, by homo-Arg is meant L-homoarginine , by D-homo-Arg is meant D-homoarginine, by Acp is meant ε-aminocaproic acid, by Chg is meant L-α-cyclohexylglycine, and by alla-Thr is meant L-allothreonine. Additionally, by Cha is meant βcyclohexyl-alanine, by Me is meant methyl ($CH_3$), by Orn is meant ornithine, by pyro-Glu is meant the pyroglutamyl group, by Met(O) and D-Met(O), are meant the sulfoxides derived from L- and D-methionine, respectively, by L-Dopa is meant 3-(3,4-dihydroxyphenyl)-L-alanine, and by Bpa is meant 4-benzoyl-phenylalanine.

The symbolism and abbreviations used are otherwise those recommended by the IUPAC-IUB Joint Commission Biochemical Nomenclature, ("Nomenclature and Symbolism for Amino Acids and Peptides, Recommendations 1983", 1985, J. Biol. Chem. 260:14–42). As is conventional, these same symbols are used to define the corresponding residues of the amino acids when they are linked to a peptide chain. Where the amino acid residue has isomeric forms, it is the L-form of the amino acid that is represented unless otherwise expressly indicated. In accordance with conventional representation, the amino group of the N-terminus of each peptide appears to the left and the carboxy group at the C-terminus to the right.

Besides the amino acid substitutions suggested above, other methods of improving transport of the polypeptide across the blood-brain barrier, such as chemical modification of the polypeptide may be employed. In any chemical modification procedure, the polypeptide may first be attached to its receptor in order to protect and maintain the receptor-binding site structure during the chemical modification process, which can comprise, for example, cationization or glycosylation.

Cyclic Peptides

The invention also utilizes as a preferred subgroup within the IGF functional derivatives described above, cyclic peptides, preferably of 5–40 amino acid residues, and most preferably of 6–25 amino acid residues. Such peptides are preferably modeled after the looped domains of the IGF molecules. Such loops may be a consequence of natural disulfide bond formation, while others are a consequence of the folding of the protein as it achieves a minimal energy conformation or a receptor-induced conformation to permit binding. As stated above, cyclization can be effected by joining the amino and carboxyl ends of a linear peptide, either directly to form an amide (lactam) bond (Example 14), or by disulfide bond formation employing terminal cysteine groups. Any internal cysteine groups present are preferably selectively blocked before cyclization and may be unblocked afterward using well-established procedures (Example 13). Alternatively, internal cysteines may be replaced by an amino acid which would be expected to have a minimal influence on peptide conformation, e.g. alanine, which is frequently used in scanning mutagenesis studies.

Examples of preferred cyclic peptides include those derived by cyclization of the following monomeric peptides via disulfide bond formation of the terminal cysteine groups:

| | |
|---|---|
| CALLETYCATPAKSEC | (SEQ ID NO:17) |
| CTYCATPAKSEC | (SEQ ID NO:57) |
| CEPYCAPPAKSEC | (SEQ ID NO:58) |
| CTYCAPAKSEC | (SEQ ID NO:59) |
| CALLETDYCATPAKSEC | (SEQ ID NO:47) |
| CTDYCATPAKSEC | (SEQ ID NO:48) |
| CTDYCAPAKSEC | (SEQ ID NO:49) |
| CTYTAPAKSEC | (SEQ ID NO:60) |
| CALLETYATPAKSEC | (SEQ ID NO:61) |
| CRRLEMYCAPLKPAKSAC | (SEQ ID NO:62) |
| CGYGSSSRRAPQTC | (SEQ ID NO:63) |
| CYFNKPTGYGC | (SEQ ID NO:64) |
| CYFNKPTGYGSSSRRAPQTC | (SEQ ID NO:65) |
| CKPTGYGSSSRC | (SEQ ID NO:66) |

An example of a cyclic peptide formed by amide bond formation is the following:

Cyclic (TYCAPAKSE) (SEQ ID NO:70).

Examples of preferred cyclic peptides based on looped domains of the IGF-I and IGF-II molecules are the following:

---

IGF I (SEQ ID NO: 1)
GPETLCGAELVDALQFVCGDRGFYFNKPTGYGSSSRRAPQTG
IVDECCFRSCDLRRLEMYCAPLKPAKSA

LOOP PEPTIDES PROPOSED:

1. Using Cys present in IGF-I.

| | | | |
|---|---|---|---|
| a) | CGCELVDALQFVC | 6-18[1] | (SEQ ID NO: 18) |
| b) | CDLRRLEMYC | 52-61 | (SEQ ID NO: 19) |
| c) | CCFRSCDLRRLEMYC | 47-61 | (SEQ ID NO: 20) |
| d) | CDLRRLEMYCCPLKPAKSE | 52-70 | (SEQ ID NO: 21) |
| e) | CCFRSC | 47-52 | (SEQ ID NO: 22) |
| f) | CFRSC | 48-52 | (SEQ ID NO: 23) |
| g) | CGCELVDALQFVC CCFRSCDLRRLEMYC | 6-18 47-61 | (SEQ ID NO: 18) (SEQ ID NO: 20) |

2. Using extra Cys.

| | | | |
|---|---|---|---|
| h) | CGPETLC | C+1-6 | (SEQ ID NO: 26) |
| i) | CGYGSSSRRCPQTGIVDEC | C+30-47 | (SEQ ID NO: 27) |
| j) | CGDRGFYFNKPTC | 21-31+C | (SEQ ID NO: 28) |
| k) | CCPLKPAKSAC | 61-70+C | (SEQ ID NO: 29) |
| l) | CDLRRLEMY*APLKPAKSAC[2] | 52-70+C | (SEQ ID NO: 30) |

[1]Numbers refer to position of amino acids in corresponding naturally occurring IGF-I.

[1] Numbers refer to position of amino acids in corresponding naturally occurring IGF-I.

IGF-II (SEQ ID NO: 16)
AYRPSETLCGGELVDTLQFVCGDRGFYFSRPASRVSRRSR
         |                   \
    GIVEECCFRSCDLALLETYCATPAKSE
          |_____|

LOOP PEPTIDES PROPOSED³:

1. Using Cys present in IGF-II.

a)  CGGELVDTLQFVC              9-21⁴    (SEQ ID NO: 32)

b)  CDLCLLETYC                 51-60    (SEQ ID NO: 33)

c)  CCFRSCDDLALLETYC           46-60    (SEQ ID NO: 34)

d)  CDLCLLETYCATPAKSE          51-67    (SEQ ID NO: 35)

e)  CCFRSC                     46-51    (SEQ ID NO: 22)

f)  CFRSC                      47-51    (SEQ ID NO: 23)

g)  CGGELVDTLQFVC              9-21     (SEQ ID NO: 32)
    |         \
    CCFRSCDLCLLETYC            46-60    (SEQ ID NO: 39)

2. Using extra Cys.

h)  CCYRPSETLC                 C+1-9    (SEQ ID NO: 40)

i)  CRPCSRVSRRSRGIVEEC         C+30-46  (SEQ ID NO: 41)

IGF-II (SEQ ID NO: 16)
AYRPSETLCGGELVDTLQFVCGDRGFYFSRPASRVSRRSR
         |                   \
    GIVEECCFRSCDLALLETYCATPAKSE
          |_____|

LOOP PEPTIDES PROPOSED³:

j)  CGDRGFYFSRPC               21-31+C  (SEQ ID NO: 42)

k)  CCTPAKSEC                  60-67+C  (SEQ ID NO: 43)

l)  CDLCLLET*ATPAKSEC          51-67+C  (SEQ ID NO: 44)

²*denotes deletion of an amino acid from the corresponding position of naturally occurring IGF-I or IGF-II.
³Some of the following peptides contain an Ala--->Cys substitution.
⁴Numbers refer to position of amino acids in corresponding naturally occurring IGF-II.

² * denotes deletion of an amino acid from the corresponding position of naturally occurring IGF-I or IGF-II.
³ Some of the following peptides contain an Ala→Cys substitution.
⁴ Numbers refer to position of amino acids in corresponding naturally occurring IFF-II.

Retro-inverso Peptides

A retro-isomer of a peptide is defined by a reversal of the direction of the peptide bond while maintaining the side-chain topochemistry. In retro-inverso peptides, D-amino acids are substituted for L-amino acids to retain the overall conformation for biological response and receptor binding similar to the native peptides (Hayward et al., Peptides 1974: Proc. 13th Eur. Peptide Symp., ed. Y. Wolman, pp. 287–297; Goodman et al., Acc. Chem.Res. 12:1–7 (1979)). It has been shown that the retro-inverso peptides introduced well defined conformational constraints and showed limited biodegradation by endopeptidases.

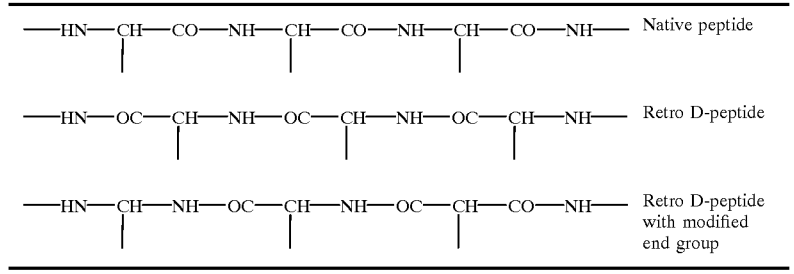

The reversal of the amino- and carboxyl termini in the retro D-peptides reduces the activity in cases where the terminal group was involved in activity. Modifications may be made at the carboxy- terminus by introducing a 2-alkylmalonate derivative and a 2-alkyl substituted geminal diamine at the amino- terminus. These groups may also be used as bridging residues when a partial or single amide modified retro-inverso segment is incorporated in a native sequence. Partial and selected single amide modified retro peptides may be used to modify the biological activity. Examples of different retro-inverso peptides are depicted here in a general sequence.

| | |
|---|---|
| gAA -- AA -- AA -- AA -- AA -- mAA | End to end modification |
| gAA -- AA -- AA --mAA -- AA -- AA | Partial modification |
| gAA -- mAA -- AA -- AA -- AA -- AA | Single amide modification | gAA=2-substituted geminal diamine amino acid surrogate mAA=2-alkyl malonate amino acid surrogate AA=L-, D- or unusual amino acid based on the design Retro-inverso peptides are synthesized both by the solution phase segment condensation method and the solid phase method. A general procedure for preparing a geminal diamino and malonyl derivative of alanine is given below.

Synthesis of gAla:

Z—HN—CH(CH$_3$)—CONH.NH$_2$ → Z—HN—CH(CH$_3$)—CO—N$_3$ →

Z—HN—CH(CH$_3$)—N=C=O → Z—HN—CH(CH$_3$)—NH.Boc →

Z—HN—CH(CH$_3$)—NH$_2$

Synthesis of mAla:

C$_2$H$_5$OOC—CH$_2$—COOC$_2$H$_5$ → C$_2$H$_5$OOC—CH(CH$_3$)—COOC$_2$H$_5$ →

HOOC—CH (CH$_3$)—COOC$_2$H$_5$

Proposed sequences: The retro-inverso peptides of the following fragments of IGF-I and IGF-II can be made following generally known peptide procedures. Numbers denote the corresponding amino acid positions of full-length IGF-I (SEQ ID NO:1), or of full-length IGF-II (SEQ ID NO:16), respectively.

```
IGF-I:
GPETL CGAEL VDALQ FVCGD RGFYF      1-25
      AEL VDALQ FVCGD RGFYF        8-25
GPETL CGAEL VDALQ                  1-15
GPETL CGAEL                        1-10
            VDALQ FVCGD RGFYF     11-25
                  FVCGD RGFYF     16-25
RGFYF NKPTG YGSSS RRAPQ TGIVD     21-45
                  RRAPQ TGIVD     36-45
            YGSSS RRAPQ TGIVD     31-45
      NKPTG YGSSS RRAPQ TGIVD     26-45
      NKPTG YGSSS RRAPQ           26-40
RGFYF NKPTG YGSSS                 21-35
      SCDLR RLEMY CAPLK PAKSA     51-70
            RLEMY CAPLK PAKSA     56-70
                  CAPLK PAKSA     61-70
      SCDLR RLEMY CAPLK           51-65
      SCDLR RLEMY                 51-60
            RLEMY CAPLK           56-65
IGF-II:
VCGDR GFYFS RPSSR INRRS RGIV      20-44
      GFYFS RPSSR INRRS RGIV      26-44
            RPSSR INRRS RGIV      31-44
      GFYFS RPSSR INRRS           26-40
```

```
        -continued
VCGDR GFYFS RPSSR                 20-35
CFRSC DLALL ETYCA TPAKS E         47-67
      LALL ETYCA TPAKS E          53-67
           TYCA TPAKS E           58-67
CFRSC DLALL ETYCA                 47-61
      DLALL ETYCA                 52-61
```

Uses of the Peptides

As described more fully below, the present invention provides novel uses of IGF-I and IGF-II and their functional derivatives, and of IGF-I, IGF-II and their functional derivatives in combination with other substances which may provide additive or synergistic effects as agents for the treatment of diseases or disturbances characterized by an increased risk of retinal neuronal cell death. The bioactivity of each polypeptide (or combination of polypeptides) of the invention may be conveniently assayed by a cultured retinal cell assay, which is described in detail below. This assay discloses previously unknown bioactivity of IGF-I and a functional derivative of IGF-II. The routine application of this assay, by one skilled in the art, can be used to discover other molecules which have activity that is additive or synergistic with that of IGF-I, as well as therapeutically useful functional derivatives of IGF-I or IGF-II. Thus, the peptides of this invention should be useful for administration to humans and other mammals who suffer from retinal diseases or disturbances characterized by increased risk of retinal neuronal cell death.

The formulations of this invention are useful for parenteral administration, for example, intravenous, subcutaneous, intramuscular, intraorbital, intraocular, ophthalmic, topical, intranasal and aerosol administration. The compositions can be formulated for parenteral administration to humans or other mammals in therapeutically effective amounts (e.g., amounts which eliminate or reduce the patient's pathological condition) to provide therapy for the retinal diseases described above.

The compounds provided herein can be formulated into pharmaceutical compositions by admixture with pharmaceutically acceptable nontoxic excipients and carriers. As noted above, such compositions may be prepared for use in parenteral administration, particularly in the form of liquid solutions or suspensions; for ophthalmic administration, particularly in the form of drops or ointments.

The compositions may conveniently be administered in unit dosage form and may be prepared by any of the methods well known in the pharmaceutical art, for example, as described in *Remington's Pharmaceutical Sciences*. Formulations for administration may contain as common excipients sterile water or saline, cyclodextrans, polyalkylene glycols such as polyethylene glycol, oils of vegetable origin, hydrogenated naphthalenes and the like. In particular, biocompatible, biodegradable lactide polymer, lactide/glycolide copolymer, or polyoxyethylene-polyoxypropylene copolymers may be useful excipients to control the release of the peptides Other potentially useful delivery systems for these peptides include ethylene-vinyl acetate copolymer particles, osmotic pumps, implantable infusion systems, and liposomes. Formulations for administration may include a stabilizing agent, such as human serum albumin, as well as a permeation enhancer, such as glycocholate. In addition, the compounds may be provided for ophthalmic administration in the form of ointments containing the active compound together with common excipients such as propylparaben, anhydrous liquid lanolin, mineral iol, and white petrolatum.

The concentration of the compounds described herein in a therapeutic composition will vary depending upon a number of factors, including the dosage of the drug to be administered, the chemical characteristics (e.g., hydrophobicity) of the compounds employed, and the route of administration. In general terms, the compounds of this invention may be provided in an aqueous physiological buffer solution or ointment containing about 0.1 to 10% w/v compound for parenteral or ophthalmic administration. Typical dose ranges are from about 1 µg/kg to about 1 g/kg of body weight per day: a preferred dose range is from about 0.01 mg/kg to 100 mg/kg of body weight per day. The preferred dosage of drug to be administered is likely to depend on such variables as the type and extent of progression of the retinal disease, the overall health status of the particular patient, the relative biological efficacy of the compound selected, the formulation of the compound excipients, and its route of administration.

The present invention will be further illustrated by the following examples. These examples are not to be construed as limiting the scope of the invention, which is to be determined solely by the appended claims.

EXAMPLES

Recombinant human IGF-I and IGF-II, as well as several chemically synthesized peptides consisting of partial sequences of IGF-I and IGF-II can be obtained from commercial sources as indicated in Table 1 or by direct chemical synthesis (see footnotes 5–7).

Example 1

To determine whether IGF-1 acts to promote survival of retinal neuronal cells, dissociated cultures of avian retina were prepared from animals at various developmental ages and the number of cells present in the cultures, following incubation for 48 hours in the presence or absence of IGF-I, was measured.

Figure 1:
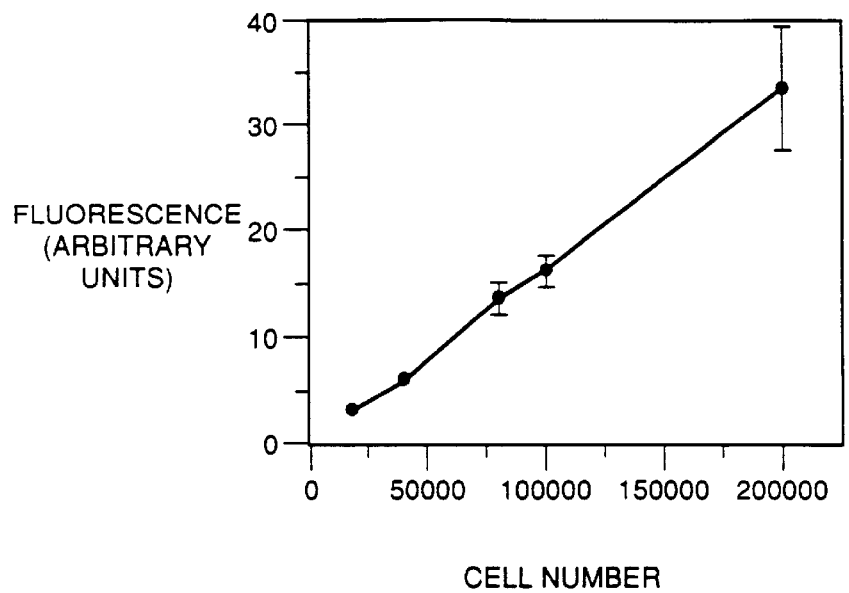
FIG. 1 is a graph illustrating the linearity of the calcein survival assay.

Retinas were dissected from embryonic chicks, dissociated by enzymatic digestion and cultured in vitro in defined insulin/serum-free medium according to Sato et al. (1979, Proc. Natl. Acad. Sci. USA 76:514–517). The number of cells in culture was measured using the vital stain calcein-AM. All cells are permeable to calcein-AM, but only live cells are capable of converting this compound into a fluorescent derivative detectable by ordinary methods. In the first experiment, calcein-AM (6 µM) was added to different cultures of retinal cells and the relationship between the level of fluorescence and the number of cells was determined. This relationship was found to be linear as shown in FIG. 1, demonstrating that this assay is useful for examining the effect of compounds on the survival of cells in culture.

Figure 2:
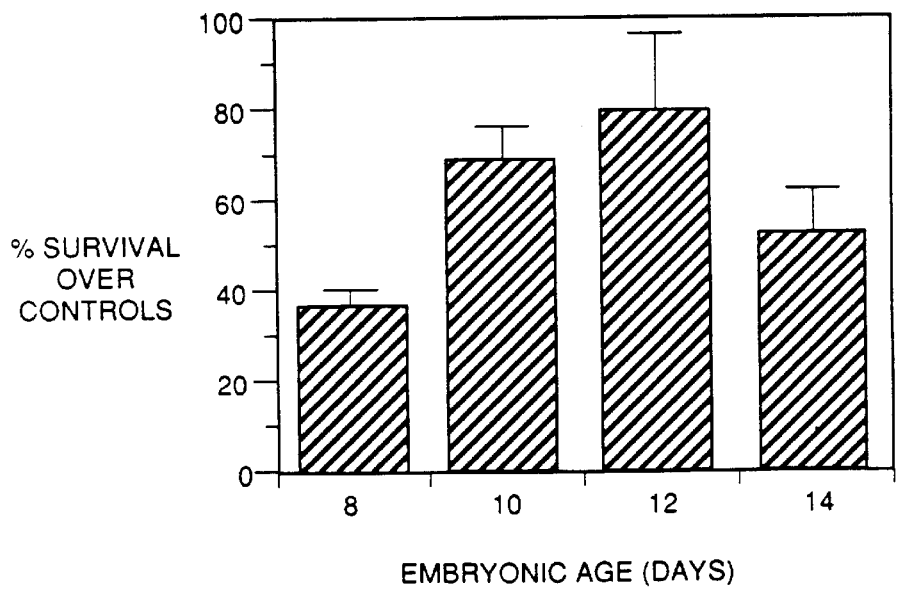
FIG. 2 is a histogram illustrating the survival-promoting effect of IGF-I on populations of retinal neurons cultured at various embryonic ages.

In the next experiment, IGF-I was added to half of the cultures at a final concentration of 100 nM, and the number of cells remaining at 48 hours post-treatment was measured using the calcein-AM assay described above. The results are presented in FIG. 2. IGF-I uniformly enhanced the survival of cells (by 20–60%) in retinal neuronal cultures obtained from embryos at 8, 10, 12 and 14 days of age, compared to control, untreated cultures.

Example 2

Figure 3:
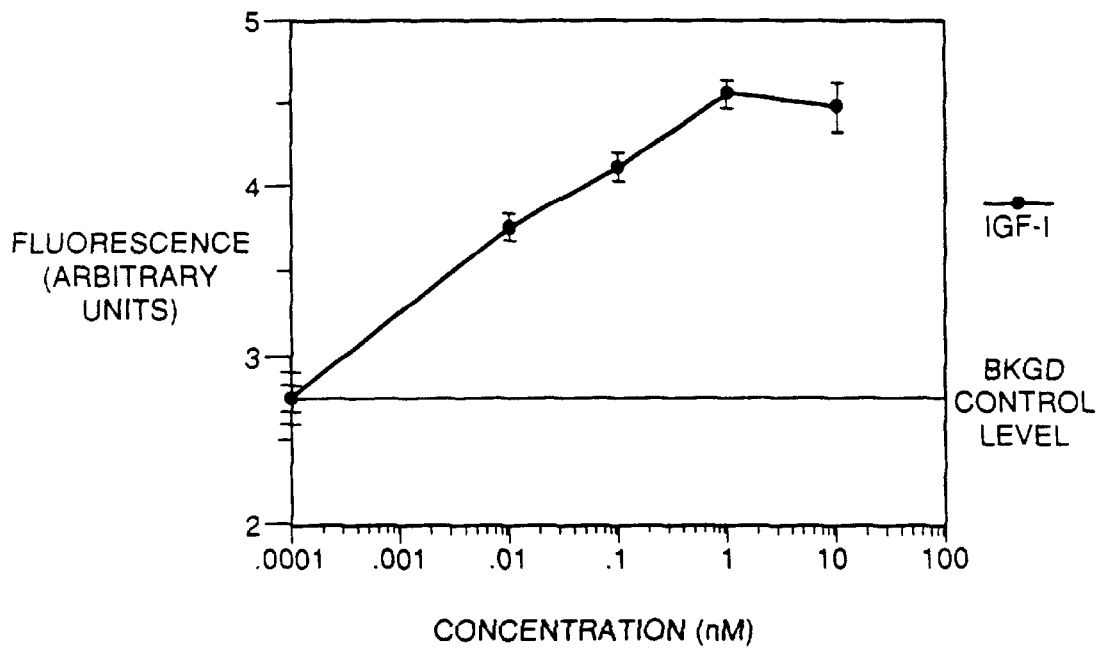
FIG. 3 is a graph illustrating the relationship between the concentration of IGF-I and the survival of a population of retinal neurons cultured from embryonic retina.
Figure 4:
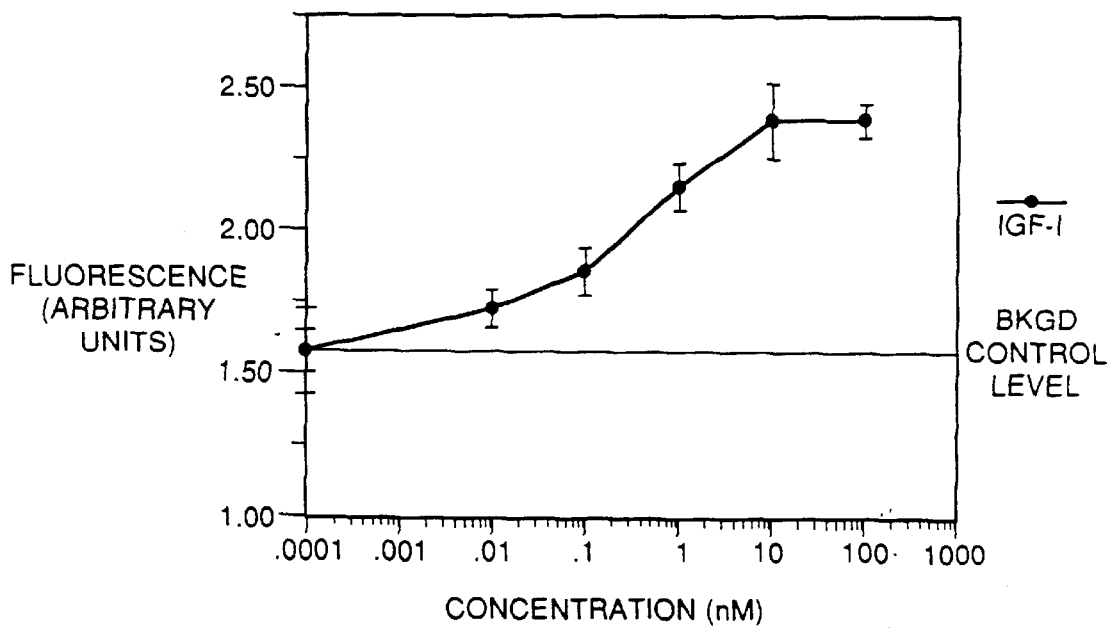
FIG. 4 is a graph illustrating the relationship between the concentration of IGF-I and the survival of a population of retinal neurons cultured from postnatal retina.

To determine the concentration of IGF-I required to promote survival of pre- or postnatal retinal neurons in culture, the following experiments were carried out: Retinal neurons were prepared from dissociated retina obtained from 10 day old chick embryos, or from adult postnatal day 6 rats as described above. Cultures were incubated in the presence of increasing concentrations of IGF-I and the number of cells surviving at 48 hours post-treatment was measured in the calcein-AM assay. The data are presented in FIGS. 3 and 4 and demonstrate that IGF-I acts both pre- and postnatally to promote survival of retinal neurons in culture in a dose-dependent manner. Based upon previously published data, the concentrations of IGF-I that promote neuronal cell survival in our experiments are consistent with the fact that IGF-I is acting through its own receptor (Karey et al., 1988, In Vitro Cell. Dev. Biol. 24:1107–1113; Ballard et al., 1988, Biochem. J. 249:721–726).

Example 3

To determine whether IGF-I affects retinal neurite regeneration, a population of neurons prepared from dissociated retina was cultured in defined insulin/serum-free media in the presence or absence of 100 nM IGF-I. Cultures were examined by phase contrast microscopy at 2–4 days following IGF-I treatment. FIG. 5 illustrates that IGF-I treated cultures contained more cells with neurites than untreated control cultures indicating that IGF-I affects axonal regeneration in retinal neurons.

Example 4

To determine whether retinal survival could be enhanced when incubated in the presence of functional derivatives of IGF-I and IGF-II, a linear fragment of IGF-II that is relatively conserved within both IGF-I and IGF-II, was tested in our assay. The fragment contained a sequence of 14 amino acids from IGF-II (amino acids 54–67, wherein the amino terminal amino acid of IGF-II is number 1). This fragment, hereinafter termed IGF-II (54–67), was added to a population of neurons prepared from dissociated rat retina at a final concentration of 100 µM, and was found to promote retinal neuronal cell survival as demonstrated in FIG. 6.

Example 5

To determine whether IGF-I or IGF-II (54–67) could specifically promote survival of the photoreceptor subpopulation of cells in rat retinal neuronal cultures, the following experiments were carried out: The monoclonal antibody Rho42, which binds to an antigenic epitope within the extracellular domain of rhodopsin expressed on the surface of rod photoreceptor cells (Molday and MacKenzie, 1983, Biochemistry 22:653), was used in this assay. Postnatal rat retinal neuronal cultures were incubated in the presence or absence of 100 nM of IGF-I for 48 hours. Cells were harvested and reacted with Rho42 to which a fluorescent label had been added. Slides were prepared and the level of fluorescence in the cultures was qualitatively assessed using a fluorescence microscope. It is clear from FIG. 7 that IGF-I treated cultures exhibited an increased level of fluorescence compared to untreated cultures, demonstrating that IGF-I promotes survival of the photoreceptor subpopulation of cells in postnatal rat retinal neuronal cultures.

To quantitate this assay, we developed a cell-based Rho42 ELISA test as follows: Several postnatal rat retinal cultures containing different numbers of cells, were incubated for 2–4 days following which cultures were fixed and immunolabelled with either the Rho42 monoclonal antibody, or the nonspecific monoclonal antibody P3, secreted by the myeloma cell line P3X6Ag8. Antibody binding was detected using a secondary antibody labelled with horseradish peroxidase and a chromogenic substrate O-phenylenediamine (OPD), having a maximum absorption wavelength of 490 nm. The level of absorption of light at 490 nm measured in the cultures is therefore directly related to the amount of primary antibody that originally bound to the cells. In FIG. 8 it can be seen that there is a linear relationship between the level of absorption at 490 nm and the number of cells in each culture. In addition, the assay is specific for photoreceptor cells because only Rho42 reacted with the cells, compared with P3 which did not.

Next, rat retinal neuronal cultures were incubated in the presence of IGF-I or IGF-II (54–67) for 48 hours following which they were subjected to the cell-based ELISA test as described above. The results are presented in FIG. 9. Both IGF-I and IGF-II (54–67) promoted the survival of photoreceptor cells by 20–30% compared with control untreated cultures.

Example 6

Cationization is a process by which free carboxyl groups of acidic amino acid residues on a polypeptide (i.e., aspartic acid and glutamic acid residues) are modified in order to increase the net positive charge on the polypeptide. The process of cationization has been used to enhance the cellular uptake of large molecules such as albumin and horseradish peroxidase into mouse fibroblast cells (Shen et al., 1978, Proc. Natl. Acad. USA 75:1872–1876). Kumagai et al. (1987, J. Biol. Chem. 262:15214–15219) used intact microvessels from bovine brain that are reportedly a model system for measuring transport across the blood-brain barrier and demonstrated that uptake of cationized albumin by isolated bovine brain microvessels was enhanced when compared with uptake of native albumin.

For global modification of free carboxyl groups, the polypeptide (e.g., IGF-I, IGF-II or a functional derivative) can be reacted with excess hexamethylenediamine (HMD) (15.5 g/g total protein) for 30 minutes at room temperature, followed by covalent coupling of HMD with 1-ethyl-3[-3-dimethyl-aminopropyl] carbodiimide hydrochloride (EDAC) (1.0 g/g total protein) for 3 hours at room temperature. Unreacted species may be removed by filtration using Centricon-3 MPS-1 separation devices (Amicon, Danvers, Mass.) or ion exchange chromatography. The purified polypeptide may be analyzed using isoelectric focusing to determine the amount of cationization.

If the global modification is used on a polypeptide that is a ligand which binds to a cell surface receptor, and the modification produces a molecule lacking biological activity, the cationization process may be repeated as described above except that the polypeptide would be pre-bound to an appropriate receptor prior to cationization, in order to protect the receptor-binding site on the polypeptide. This protection procedure can be carried out as follows:

First, tissue, e.g., brain, containing receptors for the polypeptide of interest (e.g., IGF-I) is prepared. [Alternatively, recombinant receptor can be used in place of tissue-derived receptor.] Brain tissue containing the cerebral cortex is dissected from adult rats and homogenized at low power for 5 minutes in a homogenizer (e.g., a Brinkman Polytron homogenizer) containing 50 volumes of ice-cold buffer consisting of 10 mM HEPES, 0.5% BSA, 0.0125% NEM, 0.025% bacitracin, and 100 KIU/ml aprotinin, pH 7.6 (Bohannon et al., 1986, Endocrinology 119:943–945). Following homogenization, the tissue is collected by centrifugation at 7800×g for 20 minutes and resuspended in 10 volumes of assay buffer.

Next, the tissue is incubated with the polypeptide ligand for 2 hours at 4° C. to permit receptor binding. The reaction mixture is brought to room temperature, and the cationization procedure is carried out using HMD and EDAC as described above. The reaction mixture is then centrifuged at 16,000 rpm at 4° C. for 30 seconds in an SS34 rotor in a Sorvall RC5B centrifuge. The supernatant is discarded and the pellet is washed three times in phosphate buffered saline with bovine serum albumin (1 mg/ml). The pellet is resuspended in 100 mM acetic acid and incubated for 10 minutes at 4° C. to release the cationized polypeptide from its receptors. After centrifugation again at 16,000 rpm, the supernatant, which contains the released cationized polypeptide, is pH-neutralized with NaOH. It may then be analyzed by isoelectric focusing, or any appropriate assay for biological activity.

Example 7

An alternative to the global modification method is to couple polylysine to at least one free carboxyl group on the polypeptide (such as IGF-I, IGF-II or a functional derivative of either) with or without receptor protection as described above in Example 6. The procedure follows the method of Shen et al. (1978, Proc. Natl. Acad. Sci. USA 75:1872–1876). For example, polylysine, IGF-I and carbodiimide are added in a 1:1:1 ratio in water or buffer for 3 hours at room temperature. The modified protein can be separated and analyzed as described above in Example 6.

Example 8

A third method for modifying protein carboxyl groups to enhance blood brain barrier transport is to form esters with diazomethane or N,N-dimethylformamide R acetals (DMF acetals), where R is dimethyl, diethyl, dibutyl, dibenzyl, etc. This type of modification rapidly forms esters from negatively charged carboxylic acid groups, thus increasing the overall positive charge. An additional benefit from this modification is that these added ester groups may be such that they increase the overall lipophilicity of the polypeptide and may be removed by intrinsic esterases in vivo to yield intact growth factor. The procedure for this modification, with or without receptor protection as described above in Example 6, is to react diazomethane or DMF acetals with the polypeptide in a 1:1 ratio in solution for 30 minutes at room temperature, followed by purification and characterization as described above in Example 6.

Example 9

A fourth method of cationization, with or without receptor protection as described above in Example 6, combines the advantages of polylysine cationization with the formation of cleavable esters to enhance blood-brain barrier transport, as well as to yield intact growth factor following transport. Polylysine may be made reactive by reaction with benzyloxyacetyl chloride followed by hydrogenation and mild esterification procedures (Hassner et al., 1978, Tet. Let. 46:4475–4478; Mihara et al., 1986, Int. J. Peptide Protein Res. 28:141–145). Alternatively, DMF acetal derivatives capable of reacting with polylysine could be used to link polylysine to free carboxy groups using ester linkages.

Example 10

A further type of polypeptide modification is glycosylation: the introduction of glucose or similar residues by reductive amination using, for example, glucose and sodium cyanoborohydride ($NaCNBH_3$). Glycosylation of proteins has been shown to enhance the cellular uptake of these proteins and may prove useful for improving blood-brain barrier transport. The procedure for glycosylation, with or without receptor protection as described in Example 6, is based on the method of Schwartz et al., (1977 . . . ), wherein a polypeptide such as IGF-I, IGF-II, or a function derivative of either is combined with glucose and NaCNBH$_3$ in a molar ratio of 1:300:1600 in 200 mM phosphate buffer at pH 7.0 for at least 24 hours at 37° C. Unreacted entities may be removed as described in Example 6, or with lectin affinity chromatography. In previous studies using glycosylated albumin, the modified albumin was taken up by rat epididymal microvessels at a greater rate than was native albumin (Williams et al., 1981, Proc. Natl. Acad. Sci. USA 78:2393–2397).

Example 11

To determine whether IGF-I, IGF-II, and IGF-III can promote the survival of retinal neuronal cells, dissociated cultures of postnatal rat retina were prepared and assayed for the total number of cells present after incubation in the presence or absence of IGFs. Retinas were dissected from postnatal day 6 rats, dissociated by enzymatic digestion and seeded at a density of $6.25 \times 10^4$ cells/cm$^2$ in defined insulin/serum-free media (Bottenstein et al., 1979, PNAS 76:514–517). These cultures are heterogenous, comprised of at least five independent retinal neuronal cell subpopulations, i.e., amacrine, bipolar, horizontal, photoreceptor and ganglion cells. Cultures were incubated in the presence or absence of 100 nM of each of the IGFs. The total number of cells remaining after 4 days was assayed by incubation with the vital stain calcein-AM at 6 uM. This compound is taken up by all cells but can only be converted to a fluorescent derivative by live cells. The relationship between cell number and relative flourescence is linear, indicating that this assay can be used to assess relative differences in cell numbers. FIG. 10 is a graph illustrating that in IGF-I, IGF-II, and IGF-III treated cultures, the relative fluorescence units obtained were higher than that found for untreated control cultures. These data indicate that IGF-I, IGF-II, and IGF-III increase the total number of postnatal rat retinal neuronal cells surviving over untreated cultures.

Example 12

To determine whether linear peptide derivatives of IGFs can support the survival of retinal neuronal cells, dissociated cultures of postnatal rat retina were prepared and assayed for the total number of cells present after incubation in the presence or absence of peptides (100 uM). Retinal neuronal cell cultures were prepared as described in Example 11 and the total number of cells surviving analyzed analogously. Peptides were derived from the amino acid regions 7–30 and 55–70 of IGF-I and IGF-III and the region within IGF-II, amino acids 54–67. Retinal neuronal cultures treated with the peptides IGF-II 54–67 (ALLETYCATPAKSE) (SEQ. ID No: 13); IGF-II (54–67 with D-Y at 59) (SEQ ID NO:45); IGF-II (54–67 with serine substituted at 60) (SEQ ID NO:71); IGF-II (58–67) (SEQ ID NO:68); IGF-II (58–67 with D-Y at 59) (SEQ ID NO:46); IGF-I and IGF-III (7–30; serine substituted at 18: GAELVDALQFVSGDRGFYFNKPTG) (SEQ ID NO:73); IGF-I and IGF-III (55–70: RRLEMYCAPLKPAKSA) (SEQ ID NO:67); EALLETYCATPAKSE (SEQ ID NO:36); TYCAPAKSE (SEQ ID NO:70); TdYCAPAKSE (SEQ ID NO:50); iodinated TYCAPAKSE (SEQ ID NO:25); ETQ-CATPAKSE (SEQ ID NO:72); EPYCAPPAKSE (SEQ ID NO:69); YCAPAKSE (SEQ ID NO:54); YCAPA (SEQ ID NO:55); TYCAPA (SEQ ID NO:56); CATPAKSE (SEQ ID NO:53); CAPAKSE (SEQ ID NO:24) and APSTCEYKA (SEQ ID NO:38) gave higher fluorescence values than untreated cultures. These data indicate that these peptides increased the total number of cells surviving within dissociated preparations of postnatal rat retinal neuronal cultures relative to untreated cultures (FIG. 11).

Table 5 lists peptides which were tested and did not increase the relative fluorescence units above those found for untreated cultures. While it is not a priori predictable from their structure, a high percentage of the peptides listed herein are effective for the method of the invention, and can be identified by the screening methods described herein, and by methods known to those skilled in the art.

Novel peptides of this example were prepared by solid phase peptide synthesis using methods well-known to those skilled in peptide synthesis. They are described and claimed in assignee's coassigned patent application, U.S. Ser. No. 07/869,913, filed Apr. 15, 1992.

Example 13

Part 1:
Synthesis of CALLETYCATPAKSEC (SEQ ID NO:17)
The compound CALLETYCATPAKSEC (SEQ ID NO:17) was prepared by the solid phase method of peptide synthesis on a Milligen BioSearch Model 9600 Peptide Synthesizer.
0.5 gm (0.46 mM/gm) of Fmoc-Cys (S-triphenylmethyl)-p-alkoxybenzyl alcohol resin (Advanced ChemTech) was placed in the reaction vessel and was sequentially allowed to react with 1.0 mM solutions of 1) Fmoc-Glutamic acid-γ-t-butyl ester
2) Fmoc-Serine-t-butyl ether
3) ε-t-butyloxycarbonyl-Fmoc-Lysine
4) Fmoc-Alanine
5) Fmoc-Proline
6) Fmoc-Threonine-t-butyl ether
7) Fmoc-Alanine
8) S-acetamidomethyl-Fmoc-Cysteine
9) Fmoc-Tyrosine-t-butyl ether
10) Fmoc-Threonine-t-butyl ether
11) Fmoc-Glutamic acid-γ-t-butyl ester
12) Fmoc-Leucine
13) Fmoc-Leucine
14) Fmoc-Alanine
15) S-triphenylmethyl-Fmoc-Cysteine in 1:1 DMF/DCM using benzotriazol-1-yloxytris(dimethylamino) phosphonium hexafluorophosphate (BOP) and 1-hydroxybenzotriazole (HOBT) as a coupling agent. Finally, the crude peptide CALLETYC(Acm)ATPAKSEC (SEQ ID NO:17) was removed from 0.91 gm of the resin by treatment with 10 mL of a deblocking cocktail containing 90% trifluoroacetic acid, 5% thioanisole, 3% ethanedithiol and 2% anisole. After 4.5 h of stirring the mixture was filtered and the filtrate was dried using argon and precipitated using anhydrous ether. The resulting crude peptide weighed 0.34 gm.

Part 2:
Cyclization of CALLETYC(Acm)ATPAKSEC (SEQ ID NO:17)
The crude peptide (0.3 gm) is dissolved in water (1000 mL) and the pH is adjusted to 8.4 with 50% ammonium hydroxide in water. A dilute solution (0.01 N) of potassium ferricyanide is added dropwise until a pale yellow color persists. After stirring for 2 h, the reaction is quenched by adjusting the solution to pH 4.6 with glacial acetic acid. The excess ferro- and ferricyanide ions are removed by passing through an anion-exchange column. The eluent is concentrated to 10 mL and the solution adjusted to pH 4.6. To remove the acetamidomethyl (Acm) protecting group from the internal Cys, a 0.2 M solution (4 mL) of mercury(II) acetate in 1:1 water/acetic acid is added and the reaction mixture is stirred for an hour. The resulting mixture is desalted and purified by HPLC as described above.

Example 14

Synthesis of Cyclic TYCAPAKSE (SEQ ID NO:70)

The compound cyclic TYCAPAKSE (SEQ ID NO:70) was prepared by utilizing solid phase (Milligen BioSearch Model 9600 Peptide Synthesizer) and solution phase methods.

0.79 gram (0.97 mM/gm) of p-alkoxybenzyl alcohol resin (Bachem BioScience) was placed in the reaction vessel and was sequentially allowed to react with 3.0 mM solutions of 1) Fmoc-Glutamic acid-γ-benzyl ester
2) Fmoc-Serine-O-benzyl ether
3) ε-benzyloxycarbonyl-Fmoc-Lysine
4) Fmoc-Alanine
5) Finoc-Proline
6) Fmoc-Alanine
7) S-acetamidomethyl-Fmoc-Cysteine
8) Fmoc-Tyrosine-O-benzyl ether
9) Fmoc-Threonine-O-benzyl ether in 1:1 DMF/DCM using [2-(1H-benzotriazol-1-yl)-1,1,3,3-tetramethyluroniumtetrafluoroborate (TBTU) and HOBT as a coupling agent. Each of the coupling steps was carried out as described (Example 19). The crude peptide (0.84 g) was removed from 1.82 grams of the resin by treatment with a deblocking cocktail containing 15 mL of TFA, 10 mL of DCM and 0.5 mL of water.

The peptide was dissolved in 30 mL of DMF and added to a solution of 1000 mL DMF containing 2 mL of N-methylmorpholine and 2.5 mL of diphenylphosphorazide over a period of one hour. The solvent was evaporated after overnight stirring. The crude product was dissolved in ethyl acetate (200 mL), and the solution was washed with 2% citric acid, water and 3% sodium bicarbonate. The peptide obtained after evaporation was hydrogenated for an hour using 10% Pd on activated charcoal using ethyl acetate as the solvent. The Acm group was removed from the peptide using mercury (II) acetate and purified using HPLC as described above.

TABLE 1

IGF PEPTIDE SEQUENCES

| Peptide Name | Sequence | Source | Cat. # |
|---|---|---|---|
| Human IGF-I (Somatomedin-C) | GPETL CGAEL VDALQ FVCGD RGFYF NIKPTG YGSSS-RRAPQ TGIVD ECCFR SCDLR RLEMY CAPLK PAKSA (SEQ ID NO: 1) | AMGEN[5] | 14010 |
| Human IGF-I (Somatomedin-C) | GPETL CGAEL VDALQ FVCGD RGFYF NKPTG YGSSS-RRAPQ TGIVD ECCFR SCDLR RLEMY CAPLK PAKSA (SEQ ID NO: 1) | PENINSULA[6] | 9010 Lot 15578 |
| IGF-I(4-70) (Human Brain IGF) | TLCGAEL VDALQ FVCGD RGFYF NKPTG YGSSS-RRAPQ TGIVD ECCFR SCDLR RLEMY CAPLK PAKSA (SEQ ID NO: 2) | BMB[7] BNB[7] | Lot 88:101G Lot S:25 |
| IGF-I(24-41) | YFNKP TGYGS SSRRA PQT (SEQ ID NO: 3) | PENINSULA[6] | 7308 Lot 007942 |
|  | YFNKP TGYGS SSRRA PQT (SEQ ID NO: 3) | BACHEM[8] | PGRO 080 Lot F297 |
|  | YFNKP TGYGS SSRRA PQT (SEQ ID NO: 3) | Synthetic[9] |  |
| IGF-I(30-41) | GYGSS SRRAP QT (SEQ ID NO: 4) | PENINSULA[6] | 7306 Lot 003251 |
| IGF-I(62-70) | APLKP AKSA (SEQ ID NO: 5) | PENINSULA[6] | 7318 Lot 015726 |
| IGF-I(24-32) | YFNKP TGYG (SEQ ID NO: 6) | Synthetic[9] | 7318 Lot 105726 |
| IGF-I(24-41)-AMIDE | YFNKP TGYGS SSRRA PQT-NH₂ (SEQ ID NO: 7) | Synthetic[10] |  |
| IFG-I(33-41)-AMIDE | SSSRR APQT-NH₂ (SEQ ID NO: 8) | Synthetic[10] |  |
| 48-Acm-IGF-I(42-57)-AMIDE | GIVDE CCFRS CLDRR L -NH₂ (SEQ ID NO: 9)[Acm] | Synthetic[11] |  |
| IGF-I(33-41) | SSSRR APQT (SEQ ID NO: 10) | Synthetic[9] |  |
| IGF-I(28-41) | PTGYG SSSRR APQT (SEQ ID NO: 11) | Synthetic[9] |  |
| IGF-I(27-36) | KPTGY GSSSR (SEQ ID NO: 12) | Synthetic[9] |  |
| IGF-II(54-67) | ALLET YCATP AKSE (SEQ ID NO: 13) | PENINSULA[6] [12] | 7308 Lot 010718 |
| IGF-II(62-67) | TPAKS E (SEQ ID NO: 14) |  |  |
| IGF-II(33-40) | SRVSR RSR (SEQ ID NO: 15) | PENINSULA[6] | 7304 Lot 016905 |
| IGF-II Somatomedin-A | AYRPS ETLCG GELVD TLQFV CGDRG FYFSR PASRV SRRSR GIVEE CCFRS CDLAL LETYC ATPAK SE (SEQ ID NO: 16) | COLLABORATIVE[13] COLLABORATIVE[13] | Lot 89-0172 Lot 89-0401 |

[5]Amgen, Thousand Oaks, CA 91320
[6]Peninsula Laboratories, Belmont, CA 94002
[7]Boehringer Mannheim Biochemicals, #1276-930, Indianapolis, IN 46250
[8]Bachem, Inc., Torrance, CA 90505
[9]Synthesized on a Biosearch Solid Phase Peptide Synthesizer Model 9600 using Fmoc-Amino Acids linked to p-Alokoxybenzyl Alcohol Resins supplied by Bachem Bioscience, Inc. Philadelphia, PA 19104.

TABLE 1-continued

IGF PEPTIDE SEQUENCES

| Peptide Name | Sequence | Source | Cat. # |
|---|---|---|---|

[10]Synthesized on a Biosearch Solid Phase Peptide Synthesizer Model 9600 using 4-(2',4'-Dimethoxyphenyl-Fmoc-Aminomethyl)-Phenoxy Resin (AΦ4719) supplied by Novabiochem, AG Laufelfingen, Switzerland.
[11]Synthesized on a Biosearch Solid Phase Peptide Synthesizer Model 9600 using the resin identified in footnote [6]. Acm = Acetamidomethyl substituent on the cysteine side-chain sulfur atom.
[12]This compound is incorrectly listed in the Peninsula Laboratories catalog as "Insulin-like Growth Factor I (57-70)".
[13]Collaborative Research, Inc., Bedford, MA 01730

TABLE 2

Conservative Amino Acid Replacements

| FOR AMINO ACID | CODE | REPLACE WITH |
|---|---|---|
| Alanine | A | D-Ala, Gly, Aib, B-Ala, Acp, L-Cys, D-Cys, or delete |
| Arginine | R | D-Arg, Lys, D-Lys, homo-Arg, D-homo-Arg, Met, Ile, D-Met, D-Ile, Orn, D-Orn or delete |
| Asparagine | N | D-Asn, Asp, D-Asp, Glu, D-Gln, Gln, or delete |
| Aspartic Acid | D | D-Asp, D-Asn, Asn, Glu, D-Glu, Gln, D-Gln or delete |
| Cysteine | C | D-Cys, S-Me-Cys, Met, D-Met, Thr, D-Thr, or delete |
| Glutamine | Q | D-Gln, Asn, D-Asn, Glu, D-Glu, Asp, D-Asp or delete |
| Glutamic Acid | E | D-Glu, D-Asp, Asp, Asn, D-Asn, Gln, D-Gln, or delete |
| Glycine | G | Ala, D-Ala, Pro, D-Pro, Aib, B-Ala, Acp ar delete |
| Isoleucine | I | D-Ile, Val D-Val, AdaA, AdaG, Leu, D-Leu, Met, D-Met, or delete |
| Leucine | L | D-Leu, Val, D-Val, AdaA, AdaG, Leu, D-Leu, Met, D-Met or delete |
| Lysine | K | D-Lys, Arg, D-Arg, homo-Arg, D-homo-Arg, Met, D-Met, Ile, D-Ile, Orn, D-Orn or delete |
| Methionine | M | D-Met, S-Me-Cys, Ile, D-Ile, Leu, D-Leu, Val, D-Val or delete |
| Phenylalanine | F | D-Phe, Tyr, D-Thr, L-Dopa, His, D-His, D-Trp, Trans-3,4, or 5-phenylproline, Ada-A, AdaG, cis-3,4, or 5-phenylproline, Bpa, D-Bpa or delete |
| Proline | P | D-Pro, L-l-thiazolidine-4-carboxylic acid, D-or L-l-oxa-zolidine-4-carboxylic acid (Kauer, U.S. Pat. No. 4,511,390) or delete |
| Serine | S | D-Ser, Thr D-Thr, allo-Thr, Met, D-Met, Met(O)D-Met(O), L-Cys, D-Cys, or delete |
| Threonine | T | D-Thr, Ser, D-Ser, allo-Thr, Met, D-Met, Met(O), Val, D-Val or delete |
| Tyrosine | Y | D-Tyr, Phe, D-Phe, L-Dopa, His, D-His or delete |
| Valine | V | D-Val, Leu, D-Leu, Ile, D-Ile, Met, D-Met, AdaA, AdaG or delete |
| Tryptophan | W | D-Trp, Tyr, D-Tyr, Phe, D-Phe |
| Histidine | H | D-His, Try, D-Tyr, Phe, D-Phe |

TABLE 3

| Sequence | Resin used | Purification method* (RT) | Wt. of pure peptide(mg) | SEQ ID NO |
|---|---|---|---|---|
| TYCAT PAK | Fmoc-Lys(Boc)-resin (1.0 g, 0.63 meq/g) | I (13.8 min) | 35.9 | 51 |
| LETYC ATP | Fmoc-Pro-resin (0.5 g, 0.36 meq/g) | I (20.7 min) | 6.1 | 52 |
| CATPA KSE | p-alkoxybenzylalcohol (1.0 g, 0.97 meq/g) | II (22.8 min) | 11.6 | 53 |
| TdYCAP AKSE | Fmoc-CAPAKSE-resin (0.2 g, 0.97 meq/g) | III (13.3 min) | 9.7 | 50 |
| YCAPA KSE | Fmoc-CAPAKSE-resin (0.2 g, 0.97 meq/g) | IV (13.4 min) | 14.3 | 54 |
| YCAPA | p-alkoxybenzylalcohol (1.0 g, 0.97 meq/g) | V (9.7 min) | 16.0 | 55 |
| TYCAP A | Fmoc-YCAPA-resin (0.3 g, 0.97 meq/g) | VI (16.6 min) | 25.0 | 56 |
| CAPAK SE | p-alkoxybenzylalcohol (0.4 g, 0.97 meq/g) | IV (9.1 min) | 16.2 | 24 |
| TY(I$_2$)CAP AKSE | Fmoc-APAKSE-resin (0.31 g, 0.97 meq/g) | VII (13.4 min) | 17.9 | 25 |
| EALLE TYCAT PAKSE | Fmoc-Glu(t-Bu)-resin (0.5 g, 0.36 meq/g) | VIII (12.7 min) | 10.8 | 36 |
| ALLEK YCAKP AKSE | Fmoc-Glu(t-Bu)-resin (0.5 g, 0.36 meq/g) | IX (14.3 min) | 35.0 | 37 |

TABLE 3-continued

| Sequence | Resin used | Purification method* (RT) | Wt. of pure peptide(mg) | SEQ ID NO |
|---|---|---|---|---|
| APSTC EYKA | p-alkoxybenzylalcohol (0.5 g, 0.97 meq/g) | III | 9.9 | 38 |
| ALLET YSATP AKSE | Fmoc-Glu(t-Bu)-resin (0.4 g, 0.53 meg/g) | I (25.17) | 16.86 | 71 |
| ETQCA TPAKS E | Fmoc-Glu(t-Bu)-resin (0.72 g, 0.53 meq/g) | III (12.7 min) | 8.27 | 72 |
| GAELV DALQF VSGDR GFYFN KPTG | Fmoc-Gly-resin (0.42 g, 0.32 meq/g) | V (23.23 min) | 16.86 | 73 |

*Purification methods by HPLC:
RT = Retention time
Solvent A = water with 0.1% TFA** and B = acetonitrile with 0.1% TFA
Flow rate = 9.5 mL/min. (Waters) and 3.5 mL/min.(Vydac)
I. 0–40% of B in 40 min. Column: Waters C8
II. 0–10% of B in 40 min. Column: Waters C8
III. 5–15% of B in 15 min. Column: Vydac C8
IV. 0–10% of B in 10 min. Column: Vydac C8
V. 5–60% of B in 40 min. Column: Vydac C18
VI. 5–60% of B in 60 min. Column: Waters C18
VII. 5–40% of B in 25 min. Column: Vydac C18
VIII. 10–25% of B in 40 min. Column: Waters C8
IX. 10–30% of B in 40 min. Column: Vydac C8
**TFA = trifluoracetic acid
(I) = iodination

TABLE 4

| Sequence | Amino acid analysis Theory (Found)* | Molecular mass Calculated (Found) | SEQ ID NO: |
|---|---|---|---|
| TYCATPAK | Thr 2 (1.96); Ala 2 (2.28) Pro 1 (0.98); Tyr 1 (1.00) Lys 1 (1.04); Cys 1 | 854.14 (854) | 51 |
| LETYCATP | Glx 1 (1.02); Thr 2 (1.74) Ala 1 (1.23); Pro 1 (1.10) Tyr 1 (1.00); Leu 1 (1.14) Cys 1 | 897.16 (898) | 52 |
| CATPAKSE | Glx 1 (1.05); Ser 1 (0.99) Thr 1 (1.15); Ala 2 (2.09) Pro 1 (0.99); Lys 1 (0.87) Cys 1 | 805.00 (806) | 53 |
| TdYCAPAKSE | Glu 1 (0.86); Ser 1 (0.90) Thr 1 (1.30); Ala 2 (2.04) Pro 1 (0.86); Tyr 1 (1.00) Lys 1 (1.07) | 969.00 (970) | 50 |
| YCAPAKSE | Glu 1 (0.94); Ser 1 (0.86) Ala 2 (1.96); Pro 1 (0.93) Tyr 1 (0.93); Lys 1 (1.30) Cys 1 | 867.99 (868) | 54 |
| YCAPA | Ala 2 (2.09); Pro 1 (0.96) Tyr 1 (0.98); Cys 1 | 523.00 (524) | 55 |
| TYCAPA | Thr 1 (1.18); Ala 2 (2.00) Pro 1 (0.95); Tyr 1 (0.96) Cys | 624.00 (625) | 56 |
| CAPAKSE | Glu 1 (0.92); Ser 1 (0.88) Ala 2 (2.22); Pro 1 (1.08) Lys 1 (1.09); Cys 1 | 704.00 (705) | 24 |
| TY(I$_2$)CAPAKSE | Glx 1 (0.75); Ser 1 (0.99) Thr 1 (1.02); Ala 2 (2.00) Pro 1 (1.02); Tyr 1 (0.99) Lys 1 (1.28); Cys 1 | 1220.00 (1221) | 25 |
| EALLETYCATPAKSE | Glx 3 (3.04); Ser 1 (0.91) Thr 2 (1.84); Ala 3 (3.03) Pro 1 (0.92); Tyr 1 (0.98) Leu 2 (2.18); Lys 1 (1.19) Cys 1 | 1625.00 (1626) | 36 |
| ALLEKYCAKPAKSE | Glx 2 (2.00); Ser 1 (0.81) Ala 3 (2.96); Pro 1 (0.99) Tyr 1 (0.95); Leu 2 (2.00) Lys 3 (3.07); Cys 1 | 1551.06 (1552) | 37 |
| APSTCEYKA | Glx 1 (1.02); Ser 1 (0.97) Thr 1 (0.89); Ala 2 (2.21) Pro 1 (0.89); Tyr 1 (0.94) Lys 1 (1.14); Cys 1 | 969.00 (969) | 38 |

TABLE 4-continued

| Sequence | Amino acid analysis Theory (Found)* | Molecular mass Calculated (Found) | SEQ ID NO: |
|---|---|---|---|
| ALLETYSATP-AKSE | Glx 2 (2.05); Ser 2 (1.77) Ala 3 (3.19); Pro 1 (1.07) Tyr 1 (0.94); Leu 2 (2.17) Thr 2 (1.95); Lys 1 (1.01) | 1480.70 (1480) | 71 |
| ETQCATPAKSE | Glx 3 (2.85); Ser 1 (0.94) Thr 2 (2.18); Ala 2 (1.96) Pro 1 (0.89); Lys 1 (1.02) Cys 1 | 1164.41 (1165) | 72 |
| GAELVDALQF-VSGDRGFYFN-KPTG | Glx 2 (2.00); Ser 1 (1.15) Thr 1 (1.28); Ala 2 (2.19) Pro 1 (0.92); Tyr 1 (0.89) Lys 1 (1.05); Asp 3 (3.27) Gly 4 (4.19); Arg 1 (1.02) Val 2 (1.82); Leu 2 (1.89) Phe 3 (2.61) | 2589.31 (2589) | 73 |

*Cysteine was not determined

TABLE 5

| LINEAR DERIVATIVES | | | MODIFIED LINEAR DERIVATIVES | |
|---|---|---|---|---|
| IGF-I (54-65) | ALLETYCATPAK | (SEQ ID NO: 74) | TYSAPAKSE | (SEQ ID NO: 78) |
| IGF-II (58-65) | TYCATPAK | (SEQ ID NO: 51) | EKYCAKPAKSE | (SEQ ID NO: 79) |
| IGF-II (56-65) | LETYCATPAK | (SEQ ID NO: 75) | ALLETYMATPAKSE | (SEQ ID NO: 76) |
| IGF-II (56-63) | LETYCATP | (SEQ ID NO: 52) | ALLEKYCAKPAKSE | (SEQ ID NO: 37) |
| IGF-II (63-67) | PAKSE | (SEQ ID NO: 77) | DLALLETYSATPAKSE | (SEQ ID NO: 31) |

What is claimed is:

1. A method for promoting the survival of photoreceptors in a mammal, said photoreceptors being at risk of dying, said method comprising administering to said mammal an effective dose of Insulin-like Growth Factor-I.

* * * * *

UNITED STATES PATENT AND TRADEMARK OFFICE
CERTIFICATE OF CORRECTION

PATENT NO. : 6,310,040 B1
DATED : October 30, 2001
INVENTOR(S) : Donna Bozyczko-Coyne et al.

It is certified that error appears in the above-identified patent and that said Letters Patent is hereby corrected as shown below:

Title page,
Item [56], References Cited, OTHER PUBLICATIONS,
"Goldstein" reference, please delete "etal" and insert -- et al., -- therefor.
"Kandel" reference, please delete "etal" and insert -- et al., -- therefor.
"Zackenfels" reference, please delete "etal" and insert -- et al., -- therefor.
"Lolley" reference, please delete "etal" and insert -- et al., -- therefor.
"Daughaday" reference, please delete "etal" and insert -- et al., -- therefor.
"Faktorovich" reference, please delete "etal" and insert -- et al., -- therefor.
"LaVail" reference, please delete "etal" and insert -- et al., -- therefor.
"Hicks" reference, please delete "etal" and insert -- et al., -- therefor.
"Robbins" reference, please delete "etal" and insert -- et al., -- therefor.
"Strong" reference, please delete "etal" and insert -- et al., -- therefor.
"Miller" reference, please delete "etal" and insert -- et al., -- therefor.
"Waldbillig" reference, please delete "etal" and insert -- et al., -- therefor.
"Zick" reference, please delete "etal" and insert -- et al., -- therefor.
"Waldbillig" reference, please delete "etal" and insert -- et al., -- therefor.
"Yorek" reference, please delete "etal" and insert -- et al., -- therefor.
"Bozyczko-Coyne" reference, please delete "etal" and insert -- et al., -- therefor.
"Bozyczko-Coyne" reference, please delete "etal" and insert -- et al., -- therefor.
"Bozyczko-Coyne" reference, please delete "etal" and insert -- et al., -- therefor.
"Leschey" reference, please delete "etal" and insert -- et al., -- therefor.
"Nilsson" reference, please delete "etal" and insert -- et al., -- therefor.
"Kange" reference, please delete "etal" and insert -- et al., -- therefor.
"Lynch" reference, please delete "Et Al.," and insert -- et al., -- therefor.
"Littlewood et al.," reference, please delete "Neoruochem." and insert -- Neurochem. -- therefor.
"Massague et al.," reference, please delete "(1992)" and insert -- (1982) -- therefor.
Please insert -- Hansson, H.A., *Acta Physiol. Scand.*, Vol 126, Issued 1986 pp. 609-614. --

Column 2,
Line 48, please delete "MRNA" and insert -- mRNA -- therefor.

Column 10,
Line 6, please delete "form" and insert -- from -- therefor.
Line 10, please delete "N-alkydihydroisonicotinoyl" and insert
-- N-alkyldihydronicotinoyl -- therefor.

Column 16,
Line 65, please delete "iol" and insert -- oil -- therefor.

UNITED STATES PATENT AND TRADEMARK OFFICE
CERTIFICATE OF CORRECTION

PATENT NO. : 6,310,040 B1
DATED : October 30, 2001
INVENTOR(S) : Donna Bozyczko-Coyne et al.

It is certified that error appears in the above-identified patent and that said Letters Patent is hereby corrected as shown below:

Column 23,
Line 25, please delete "Finoc-Proline" and insert -- Fmoc-Proline -- therefor.

Columns 23-24,
Table 1: at IGF-I(4-70) (Human Brain IGF), third column, second line thereof, please delete "BNB$^7$" and insert -- BMB$^7$ -- therefor.

Signed and Sealed this

Twenty-sixth Day of October, 2004

JON W. DUDAS
*Director of the United States Patent and Trademark Office*